US010255647B2

(12) United States Patent
Rodman et al.

(10) Patent No.: US 10,255,647 B2
(45) Date of Patent: Apr. 9, 2019

(54) CONTROLLING AND COMMUNICATING WITH RESPIRATORY CARE DEVICES

(75) Inventors: Terrell Lee Rodman, Carlsbad, CA (US); Ningda Andy Dai, Carlsbad, CA (US); Patrick T. Bird, San Diego, CA (US); Paul L. Edwards, Encinitas, CA (US); Ronald F. Richard, Escondido, CA (US); Peter Armstrong, Poway, CA (US)

(73) Assignee: Caire Inc., Ball Ground, GA (US)

( * ) Notice: Subject to any disclaimer, the term of this patent is extended or adjusted under 35 U.S.C. 154(b) by 422 days.

(21) Appl. No.: 12/892,793

(22) Filed: Sep. 28, 2010

(65) Prior Publication Data

US 2011/0073107 A1    Mar. 31, 2011

Related U.S. Application Data

(60) Provisional application No. 61/246,271, filed on Sep. 28, 2009.

(51) Int. Cl.
*A61M 16/10* (2006.01)
*G06Q 50/22* (2018.01)
(Continued)

(52) U.S. Cl.
CPC ........... *G06Q 50/22* (2013.01); *A61M 16/101* (2014.02); *G06F 19/00* (2013.01);
(Continued)

(58) Field of Classification Search
CPC ................ A61M 16/10; A61M 16/101; A61M 2016/102; A61M 2016/1025;
(Continued)

(56) References Cited

U.S. PATENT DOCUMENTS 5,699,494 A * 12/1997 Colbert ................. G06F 3/1293
358/1.13
6,158,430 A * 12/2000 Pfeiffer et al. ........... 128/202.27
(Continued)

FOREIGN PATENT DOCUMENTS

CN        101500633 A     8/2009
WO    WO-2007145948 A2   12/2007

OTHER PUBLICATIONS

International Search Report dated Jun. 24, 2011, issued in connection with corresponding PCT application No. PCT/US2010/050580.
(Continued)

*Primary Examiner* — Timothy A Stanis
(74) *Attorney, Agent, or Firm* — Cook Alex Ltd.; R. Blake Johnston

(57) ABSTRACT

Disclosed are methods, systems, apparatus, and products, including a method for operating a respiratory care device that includes collecting at a respiratory care device data representative of operation of the respiratory care device, and communicating to a computing-based device external to the respiratory care device at least some of the collected data to control the operability of the respiratory care device. In some embodiments, the method may further include communicating to the respiratory care device data to controllably change one or more operation parameters of the respiratory care device to cause a change in the operation of the respiratory care device, changing the operation parameters of the respiratory care device according to the communicated data, and communicating to the external computing-based device resultant data representative of operation of the respiratory care device resulting from the controllable change to the one or more operation parameters.

18 Claims, 13 Drawing Sheets

(51) Int. Cl.
    *G06Q 10/06*     (2012.01)
    *G06F 19/00*     (2018.01)
    *G16H 40/63*     (2018.01)

(52) U.S. Cl.
    CPC ......... *G06F 19/3481* (2013.01); *G06Q 10/06* (2013.01); *G16H 40/63* (2018.01); *A61M 16/107* (2014.02); *A61M 2202/0208* (2013.01); *A61M 2202/03* (2013.01); *A61M 2205/3358* (2013.01); *A61M 2205/3368* (2013.01); *A61M 2205/3553* (2013.01); *A61M 2205/3584* (2013.01); *A61M 2205/502* (2013.01); *A61M 2205/52* (2013.01); *B01D 2259/4533* (2013.01)

(58) Field of Classification Search
    CPC .. A61M 2205/3553; A61M 2205/3584; A61M 2205/502; A61M 2205/52
    USPC .... 128/201.21, 204.21–204.23, 205.11, 920, 128/923–925
    See application file for complete search history.

(56) References Cited

U.S. PATENT DOCUMENTS

| | | | | |
|---|---|---|---|---|
| 6,305,373 | B1* | 10/2001 | Wallace et al. | 128/204.21 |
| 6,651,658 | B1* | 11/2003 | Hill et al. | 128/204.23 |
| 7,017,575 | B2* | 3/2006 | Yagi et al. | 128/205.11 |
| 7,066,173 | B2 | 6/2006 | Banner et al. | |
| 7,708,802 | B1* | 5/2010 | Deane et al. | 95/19 |
| 2002/0126036 | A1* | 9/2002 | Flaherty | A61B 5/14532 341/176 |
| 2002/0133061 | A1* | 9/2002 | Manetta | 600/300 |
| 2003/0005928 | A1* | 1/2003 | Appel et al. | 128/202.26 |
| 2003/0189492 | A1* | 10/2003 | Harvie | 340/573.1 |
| 2004/0003813 | A1* | 1/2004 | Banner et al. | 128/204.21 |
| 2005/0103354 | A1* | 5/2005 | Miyauchi | A61B 6/032 128/898 |
| 2006/0237014 | A1* | 10/2006 | Makinson et al. | 128/204.23 |
| 2008/0053441 | A1* | 3/2008 | Gottlib et al. | 128/204.23 |
| 2008/0105257 | A1* | 5/2008 | Klasek et al. | 128/203.27 |
| 2008/0120553 | A1* | 5/2008 | Bergman | H04L 67/38 715/740 |
| 2008/0185009 | A1* | 8/2008 | Choncholas et al. | 128/897 |
| 2009/0126736 | A1 | 5/2009 | Taylor et al. | |
| 2009/0131763 | A1 | 5/2009 | Taylor et al. | |
| 2009/0229610 | A1* | 9/2009 | Oates et al. | 128/204.21 |
| 2010/0051030 | A1 | 3/2010 | Richard et al. | |
| 2010/0078016 | A1* | 4/2010 | Andrieux et al. | 128/202.22 |
| 2011/0162647 | A1* | 7/2011 | Huby et al. | 128/203.14 |

OTHER PUBLICATIONS

SeQual Technologies Inc., "Eclipse & Eclipse 2 PAOS: Eclipse Data Aquisition Tool", *EDAT Users Manual*, Dec. 2008.
SeQual Technologies Inc., "EDAT software set: World's first computer based oxygen concentrator service tool", *EDAT Sales Presentation*, Dec. 2008(pricing information redacted).
The State Intellectual Property of China First Office Action, issued in Chinese Patent Application No. 201080051538.5, dated May 16, 2014.

* cited by examiner

CONTROLLING AND COMMUNICATING WITH RESPIRATORY CARE DEVICES

CROSS-REFERENCE TO RELATED APPLICATIONS

The present application claims benefit and priority to U.S. Provisional Patent Application No. 61/246,271, filed Sep. 28, 2009, and entitled "DATA RETRIEVAL AND SERVICE SYSTEM AND METHOD FOR OXYGEN CONCENTRATORS," the content of which is hereby incorporated by reference in its entirety.

BACKGROUND

The present disclosure relates to respiratory care devices, and more particularly to operating, including communicating and controlling, respiratory care devices such as oxygen concentrators, ventilators, CPAP machines, etc.

As home respiratory care devices, such as home medical oxygen concentrators, continue to evolve, they have started to progress from simple electro-mechanical devices to computer controlled systems. With this evolution, the diagnosis and repair of devices or the upgrading of devices with new software controlled functionality has become more difficult. The complexity of these new systems often makes them too complicated for traditional field technicians to service the devices efficiently. As such, technicians have to either guess at a probable cause and repair based upon best available data, or return the device to their repair shop for diagnosis by a better trained technician. These options result in taking the device out of service, creating an inconvenience for the patient using the device, and resulting in a loss of revenue for the company that owns and operates the device.

The level of expertise, training and education of personnel sent into the field to diagnose and solve problems with respiratory care devices has to be high. They not only have to know how the equipment works in normal operation but also under fault conditions. To diagnose the cause of failure or to determine if, for example, the oxygen concentrator is working properly takes months of experience and training. If an untrained or low level technician is sent on a service call, they often have to bring the device back to a trained technician for service. The untrained or low level technician may call the trained technician and try to describe the device's conditions, but this makes service calls lengthy and seldom results in fixed respiratory care devices, and the devices usually have to be sent to a skilled technician anyway. Additionally, a respiratory care device generally cannot be updated with important software changes without being returned to a skilled technician.

Also, often, a respiratory care device has a small data memory and a limited user interface that makes even trained technicians troubleshooting and diagnostic very difficult.

SUMMARY

Therefore, an objective of the present disclosure is to provide systems, methods, products, and implementations to overcome the above-identified issues.

Thus, described herein are systems, methods, products, and implementations to communicate operation data of respiratory care devices to computing-based devices to enable, for example, controlling of the respiratory care devices from remote locations.

The systems, methods, products, and implementations of the present disclosure allow unskilled or minimally skilled technicians to diagnose and repair home respiratory care devices (e.g., medical oxygen concentrators, ventilators, CPAP devices, etc.) or upgrade these devices with new software controlled functionality.

The systems, methods, products, and implementations of the present disclosure enables remotely located trained technician to see and manipulate a duplicate version of the subject respiratory care device on a local computer to thus facilitate troubleshooting and upgrading of the subject respiratory care device.

The systems, methods, products, and implementations of the present disclosure reduce the need for highly skilled technicians, reduce time to repair, and require fewer loaner respiratory care devices to replace units in the field while the malfunctioning devices are being transported for repair. If the respiratory care devices are fixed in the field then transporting units become unnecessary.

The systems, methods, products, and implementations of the present disclosure enable connecting respiratory care devices to a network (such as the public Internet) for diagnosis and repair (while still in the field), by one technician or a team of engineers and technicians anywhere in the world.

In some embodiments, the systems, methods, products, and implementations of the present disclosure include a Windows®-based machine, a system software application including one or more software modules, a troubleshooting guide, a dual port USB-Serial converter, and an oxygen concentrator.

In some embodiments, the system software relays diagnostic information from a respiratory care device to a user. In such embodiments, the system software might not try to interpret the data. The interpretation of the data may be left for the technician who may use a troubleshooting guide.

In some embodiments, the system reports all pieces of information (e.g., symptoms) that are useful for troubleshooting the respiratory care device. These pieces of information include, but are not limited to, event tables (e.g., providing a history of recorded events), real time data, real time and historical data records, firmware revisions, total number of operating hours, etc. The system software can control the connected respiratory care device to, for example, start/stop, change flow settings and control mode, adjust compressor and pressure swing adsorption cycle speed, etc. The system software may simulate certain conditions to diagnose the system. The system software also gives the ability to manipulate and change different device parameters such as, but not limited to, bolus frequency, flow data, and motor configuration. The system software can upgrade firmware, as well.

In some embodiments of the present disclosure, the system includes a respiratory care device with a serial communication, a computer (located externally and separated from the respiratory care device, and which may be located in proximity to or remotely from the respiratory care device), a communication adapter that links the respiratory care device with the computer, a network (e.g., the Internet, a private network which may be packet-based or implemented using other technologies and/or protocols, etc.) attached to the local computer, one or more other computers (e.g., remote computers), connected to the computer via a network, one or more system software modules that run on the computer, and one or more remote software modules that run on the computers The software module(s) is configured to perform one or more functions. One function may include the ability to remotely examine a data log of a respiratory care device.

Elements of the data log include, but are not limited to compressor temperature, flow rate, bolus size, and ambient pressure. Another function is to remotely examine (e.g., by a clinician/physician) the data log of the respiratory care device and medical data of the user, and to remotely change operation parameters of the respiratory care device based on the log data and/or the user's medical data.

The system may use a removable memory device (e.g., USB memory stick) to implement a software key procedure. The memory device includes one or more software modules that launch and run if the key is installed at the local computer or on the removable memory device. The one or more software modules automatically connect the local computer with the serial ports. If the ports are not setup correctly, the one or more software modules display a dialog that helps users to connect with the respiratory care device correctly. The one or more software modules automatically detect the firmware part number, version and other information of the connected respiratory care device, and upgrades the new firmware if selected. The one or more software modules continuously or periodically monitor and display all the information from the connected respiratory care device. The one or more software modules enable users to calibrate and configure the connected respiratory care device. One or more software modules enable users to start/stop the connected respiratory care device, to change flow setting and to change control mode. The one or more software modules continually record and log all the data of the connected respiratory care device to local computer memory. The one or more software modules include a remote monitoring function to transfer all data to a terminal.

With the system, method, products, and implementation of the present disclosure, a low-level technician or non-technical person can arrive, connect to the respiratory care device to the system and attempt to diagnose the problem. If the problem is not corrected immediately, the system may be connected via a network to a remote computer where a trained technician can take control of the systems and the respiratory care device, perform diagnosis, make adjustments or instruct the person on site to correct the problem. This can reduce the number of respiratory care devices that need to be returned to a trained technician for service.

With the system and method of the present disclosure, a respiratory care device may be upgraded with important software changes by low level technicians locally or remotely.

In some embodiments, a unique procedure that includes embedding a key code in the file allocation table (FAT) within a removable memory device may be used. The FAT includes a number of software upgrades that are implemented into the respiratory care device. Embedding a key code in the FAT prevents copying of the system's removable memory device that is necessary for the system application to function. It also prevents copying and controls software upgrade times.

Thus, in one aspect, a method for operating a respiratory care device is disclosed. The method includes collecting at a respiratory care device data representative of operation of the respiratory care device, and communicating to a computing-based device external to the respiratory care device at least some of the collected data to control the operability of the respiratory care device.

Embodiments of the method may include any of the features described in the present disclosure, including any of the following features.

The respiratory care device may be one of, for example, a supplemental oxygen device, a ventilator, and/or a continuous positive air pressure (CPAP) device.

The supplemental oxygen device may be one of, for example, an oxygen concentrator, and/or a device that fills gas cylinders.

The supplemental oxygen device may include the storage of liquid oxygen.

Communicating to the remote computing-based device at least some of the collected data to control the operability of the respiratory care device may include communicating to the remote computing-based device at least some of the collected data to enable determination of problems relating to the operability of the respiratory care device.

The method may further include determining one or more problems relating to the operability of the respiratory care device based on the communicated at least some of the collected data.

Communicating to the remote computing-based device at least some of the collected data to control the operability of the respiratory care device may include communicating to the remote computing-based device at least some of the collected data to enable determination of clinical modification of operation parameters to change the clinical performance of the respiratory care device.

The method may further include communicating to the respiratory care device data to controllably change one or more operation parameters of the respiratory care device to cause a change in the operation of the respiratory care device, changing the operation parameters of the respiratory care device according to the communicated data to controllably change the one or more operation parameters, and communicating to the external computing-based device resultant data representative of operation of the respiratory care device resulting from the controllable change to the one or more operation parameters.

Communicating to the respiratory care device data to controllably change the one or more operation parameters may include communicating one or more of, for example, data to change at least one parameter controlling the start and stop operation of the respiratory care device, data to change at least one parameter controlling flow setting of the respiratory care device, data to change at least one parameter controlling compressor mode of the respiratory care device, data to change at least one parameter controlling bolus frequency of the respiratory care device, and/or data to change at least one parameter controlling the pressure swing adsorption cycle of the respiratory care device.

Collecting at the respiratory care device data representative of the operation of the respiratory care device may include collecting one or more of, for example, event tables, real time data, real time and historical data records, firmware revisions, number of operating hours, oxygen concentration level values, compressor speed, measured oxygen flow, target oxygen flow, ambient pressure, oxygen product pressure, target oxygen product pressure, battery temperature, oxygen temperature, compressor temperature, electronics printed circuit board temperature, battery voltage, battery capacity, alarm threshold, electrical voltage from an external source, electrical current provided from the external source, and/or power provided by the external source.

Communicating to the computing-based device at least some of the collected data may include determining if at least one removable memory device storing data used to enable the computing-based device to communicate with the respiratory care device includes a software key stored in a file allocation table of the at least one removable memory device, preventing at least some of communication operations between the computing-based device and respiratory care device if the file allocation table of the at least one removable memory device does not include the software key, and enabling the communication operations between the computing-based device and respiratory care device if the file allocation table of the at least one removable memory device includes the software key The method may further include storing at a file allocation table of at least one removable memory device a value indicative of upgrades allowed for one or more of, for example, software components implemented on the computing-based device and/or software components implemented on the respiratory care device, and decrementing the stored value indicative of the allowed upgrades when a software upgrade is performed for one of: the software components implemented on the computing-based device and/or the software components implemented on the respiratory care device.

The method may further include applying the communicated at least some of the collected data to a troubleshooting guide to determine the problems relating to the operability of the respiratory care device.

The method may further include collecting medical data relating to a user of the respiratory care device, communicating the medical data relating to the user to the computing-based device external to the respiratory care device, and determining values of the operation parameters controlling operation of the respiratory care device based on, at least in part, the communicated data relating to the operation of the respiratory care device and the medical data.

The medical data may include one or more of, for example, the user's breathing rate, oxygen level in the user's blood, the user's heart rate, and/or temperature of the user.

In another aspect, a system is disclosed. The system includes a respiratory care device including one or more memory devices to store data representative of operation of the respiratory care device, the data being collected from the respiratory care device, and a computing-based device coupleable to the respiratory care device, the computing-based device being external to the respiratory care device. The respiratory care device is configured to communicate to the external computing-based device at least some of the collected data to control the operability of the respiratory care device.

Embodiments of the system may include any of the features described in the present disclosure, including any of the features described above in relation to the method and the features described below, including any one of the following features The external computing-based device may be configured to communicate to the respiratory care device data to controllably change one or more operation parameters of the respiratory care device to cause a change in the operation of the respiratory care device. The respiratory care device may further be configured to change the operation parameters of the respiratory care device according to the communicated data to controllably change the one or more operation parameters, and communicate to the external computing-based device resultant data representative of operation of the respiratory care device resulting from the controllable change to the one or more operation parameters.

The system may further include a communication interface interfacing the external computing-based device and the respiratory care device.

In a further aspect, a computer program product stored on a non-transitory computer readable storage medium is disclosed. The computer readable storage medium includes computer instructions that, when executed on at least one processor-based device, cause the at least one processor-based device to collect at a respiratory care device data representative of operation of the respiratory care device, and communicate to a computing-based device external to the respiratory care device at least some of the collected data to control the operability of the respiratory care device.

Embodiments of the computer program product may include any of the features described in the present disclosure, including any of the features described above in relation to the method and the system, and the features below, including the following feature.

The computer program product may further include computer instructions that further cause the at least one processor-based device to communicate to the respiratory care device data to controllably change one or more operation parameters of the respiratory care device to cause a change in the operation of the respiratory care device, change the operation parameters of the respiratory care device according to the communicated data to controllably change the one or more operation parameters, and communicate to the external computing-based device resultant data representative of operation of the respiratory care device resulting from the controllable change to the one or more operation parameters.

In yet another aspect, a method for operating a respiratory care device is disclosed. The method includes receiving at a computer-based device external to the respiratory care device data representative of operation of the respiratory care device, the data collected at the respiratory care device, and based, at least in part, on the received data representative of the operation of the respiratory care device, communicating from the computing-based device to the respiratory care device data to controllably change one or more operation parameters of the respiratory care device to cause a change in the operation of the respiratory care device.

Embodiments of the method may include any of the features described in the present disclosure, including any of the features described above in relation to the first method, the system, and the computer program product, as well as the features described below.

Details of one or more implementations are set forth in the accompanying drawings and in the description below. Further features, aspects, and advantages will become apparent from the description, the drawings, and the claims.

BRIEF DESCRIPTION OF THE DRAWINGS

Like reference numbers and designations in the various drawings indicate like elements.

DETAILED DESCRIPTION

Described herein are methods, systems, apparatus and computer program products, including a method for operating respiratory care devices that includes collecting at a respiratory care device data representative of operation of the respiratory care device, and communicating to an external computing-based device (which may be proximate to the respiratory cared device or remote from it) at least some of the collected data to control the operability of the respiratory care device. In some implementations, the communicated data may enable, for example, determination of problems relating to the operability of the device (e.g., remote diagnosis and repair of the device), setting new operation parameters to remotely change (e.g., by a doctor for therapeutic reasons) device settings, etc.

As will be described in greater details below, in some embodiments, to enable diagnosing problems and/or repairing problems, a technician may be able to modify operational or functional features of the respiratory care device to cause a change in the behavior of the device from which the technician may be able to obtain further information and insight as to the nature of any underlying problem. Accordingly, in some embodiments, the method may also include communicating to the respiratory care device data to controllably change one or more operation parameters of the respiratory care device to cause a change in the operation of the respiratory care device, changing the operation parameters of the respiratory care device according to the communicated data to controllably change the one or more operation parameters, and communicating to the external computing-based device resultant data representative of operation of the respiratory care device resulting from the controllable change to the one or more operation parameters.

As used herein, "respiratory care device" refers to a device used to aid or assist a patient with respiratory function and/or to provide supplemental oxygen to a patient. Such respiratory care devices include, for example, supplemental oxygen devices, ventilators, cough assist devices, continuous positive air pressure (CPAP) machines, etc. As used herein, "supplemental oxygen device" generally refers to a device that provides oxygen to a patient at concentrations higher than, for example, 21%. Such devices include oxygen concentrators, gas cylinder filling booster pumps, and devices including a container or liquid oxygen for patient breathing.

Figure 1:
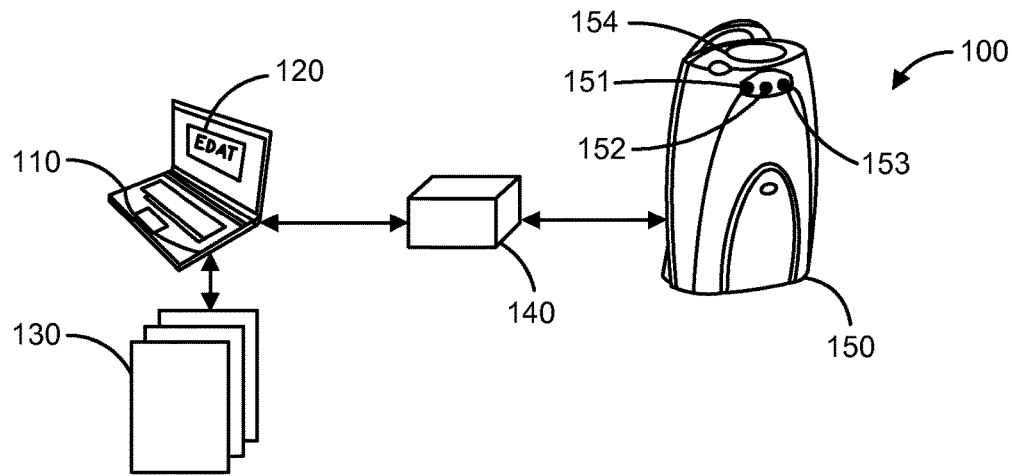
FIG. 1 is a schematic diagram of an example system for diagnosing, updating, and repairing a respiratory care device.

With reference to FIG. 1, a schematic diagram of an example embodiment of a system 100 and method for operating a respiratory care device (e.g., diagnosing, updating, controlling, repairing, etc.) is shown. The system 100 includes a computing-based device 110 in communication with a respiratory care device 150. The computing-based device 110, which is external to the respiratory care device (e.g., it is not housed within the respiratory care device) may communicate with the respiratory care device 150 via an interfacing device 140 (e.g., a modem, communication gateway, an adapter, etc.), or may communicate directly with the respiratory care device without an intermediate interfacing device. For example, communication modules (e.g., network ports, wireless or wire-based transceivers implemented at each of the computing-based device and the respiratory care device, etc.) may be used to enable communication between the devices 110 and 150.

As further shown in FIG. 1, the system 100 includes an interfacing application 120, such as the Eclipse Data Acquisition Tool (EDAT) application developed by SeQual Technologies, Inc., to process and manage data communicated from its Eclipse® oxygen concentrator, and to communicate to the respiratory care device 150 data and commands to control the operation of the respiratory care device 150 (e.g., so as to change the functional behavior of the device 150 in such a way as to provide useful information on the performance of the device and possible problems associated therewith, to change operation parameters for clinical/therapeutic reasons, etc.) Interfacing applications similar to the EDAT may be used for other respiratory care devices. In some embodiments, the application 120 is implemented, at least in part, as a software-based application comprising one or more software modules.

The application 120 is configured to execute on, for example, the computing-based device 110, to relay and present to a user data relating to the operability of the respiratory care device 150, and to receive input from users and/or other devices (e.g., at a remote care center) interacting with the application 120 and the computing-based device 110 to communicate back to the respiratory care device 150 data and commands based on the input provided by such users/devices. In some embodiments, the system software 120 does not include functionality to interpret data communicated to it from the respiratory care device 150 to determine appropriate responses (e.g., determine the nature of any problems exhibited by the operation of the respiratory care device 150). Generally, a separate troubleshooting application, or a trained user assisted by a troubleshooting manual/guide (such as a troubleshooting guide 130) identify problems and control operation of the respiratory care device 150. However, embodiments that include modules or engines to determine appropriate responses or actions from the communicated data (e.g., learning machines, such as neural nets, configured to identify problems and determine responses based on received operability data of the respiratory care device 150) are within the scope of the present disclosure.

Thus, in some embodiments, the application 120 is configured to report all pieces of information useful for troubleshooting the device 150's common symptoms. These pieces of information include, but are not limited to, event tables, real time data, real time and historical data records, firmware revisions, and total number of operating hours, oxygen concentration, actual compressor speed, target compressor speed, measured flow, target flow, ambient pressure, oxygen product pressure, target oxygen product pressure, battery temperature, oxygen temperature, compressor temperature, electronics printed circuit board temperature, battery voltage, battery capacity, electrical voltage and current from an external source, and external power.

The application 120 is further configured to control and change different device parameters such as, but not limited to, bolus frequency, flow calibration data, and motor configuration. The application 120 can upgrade firmware as well.

In some embodiments, the respiratory care device 150 includes a controller 152 (also referred to a controlling unit)

which may be implemented using one or more processor-based devices configured to generate control signals to control the various modules and components of the respiratory care device 150, such as the device's motor, air compressor, oxygen generator (for devices that include such components/modules) and other modules/components (including the components/modules described in relation to the oxygen concentrator shown in FIGS. 2 and 3). Generating appropriate control signal may be based on parameter values that are recorded, for example, in memory devices 153 coupled to the one or more processor-based device of the respiratory care device 150, including volatile memory devices (e.g., CPU registers, DRAM, cache memory, etc.) and/or non-volatile memory devices. For example, to control the operational behavior of the motor, one or more parameters values relating to the motor (e.g., a motor speed parameter) may be set by, for example, inputting parameter values via a user interface 154 located on the respiratory care device, communicating parameter values from a remote device (such as the computing-based device 110), pre-programming parameter values that are to be used in different circumstances, etc. The one or more processor-based devices of the controller 152 of the respiratory care device 150 may be configured to execute one or more computer programs to generate and/or receive data and instructions to enable modifying controllable parameter values of the respiratory care device 150, to generate control signal to control the corresponding components/modules of the device 150 whose operation is controlled through those parameter values, to collect and communicate data relating to the operation of the device 150 and/or data relating to condition of the user/patient using the respiratory care device, etc. In some embodiments, the various functionalities of the controller 152 may also be performed, for example, by using special purpose logic circuitry, e.g., an FPGA (field programmable gate array) or an ASIC (application-specific integrated circuit).

As noted, in some embodiments, the system 100 may be used to enable determination of problems associated with the respiratory care device 150. In such embodiments, and as will more particularly be described below, data relating to the operation of the respiratory care device 150 is collected at the device 150. For example, data representative of the behavior/operation of the device 150 (e.g., oxygen concentration, motor speed, various temperatures, etc.) are continually collected from the respective components/modules of the device 150 and are recorded (possibly after being processed to convert or format the data to more meaningful values) at storage areas of the memory devices 153 of the controller 152. In some embodiments, medical data pertaining to the patient (e.g., heart rate, breathing rate, etc.) may also be collected and stored at the controller 152.

Periodically or continuously, the recorded data is communicated to a computing-based device 110 on which the application 120 is implemented. A service person (technician) operating the computing-based device 110 and the application 120 is provided with data representative of the operational behavior of the respiratory care device 150. Based on that presented data, and optionally with the assistance of a manual or troubleshooting guide 130 (which may be available electronically as an application on the computing-based device 110), the technician may determine the nature of a problem that is affecting the performance of the respiratory care device. The computing-based device 110 (or a different computing-based device in communication with the computing-based device 110) may be located at a remote service center, and may be communicating with the respiratory care device through network-based communication (wireless or wire-based) through dedicated communication links (wireless or wired-based), etc. In some embodiments, the computing-based device may be situated in proximity to the respiratory based device (although the computing-based device may still be external to the respiratory care device). Such embodiments are typical in situations where field technicians arrive to service the respiratory care device. In those situations it may happen that the technician lacks the experience or skill to identify the nature of the problem, and accordingly, the technician may contact a more skilled technician at a remote service center to assist the technician to identify the problem with the particular respiratory care device. Another computing-based device used by the technician at the service center may then form a communication link with the field technician's computing-based device or directly with the respiratory care device to receive the relevant operational data and help identify the problem.

In some embodiments, to facilitate identifying the problem(s) with the particular respiratory care device, the technician (be it a field technician or a service center technician) may need to change certain operational attributes of the respiratory care device so as to obtain operation data resulting from the change to the operational attributes, which in turn can provide further insight as to the nature of the problem. For example, problems of pathway blockages may be identified by varying motor speed to see how air flow is affected by the change. To change the operational behavior of the particular respiratory care device, the technician may change operation parameters by using, for example, an interface that provides similar functionality to the interface located on the respiratory device itself. For example, and as will be described in greater details below in relation to FIGS. 7-12, the technician may be able to enter data through a graphical representation e.g., available through the interfacing application 120, of the interface of the respiratory care device.

Thus, the technician at the computing-based device may input various new parameter values via, for example, a user interface implemented through the application 120, to controllably change one or more operation parameters (affecting operational attributes) of the respiratory care device. Data representative of the desired changes to the operation parameters are then communicated to the respiratory care device. Examples of data to controllably change the operation parameters include one or more of, for example, data to change at least one parameter controlling the start and stop operation of the respiratory care device, data to change at least one parameter controlling flow setting of the respiratory care device, data to change at least one parameter controlling compressor mode of the respiratory care device, data to change at least one parameter controlling bolus frequency of the respiratory care device, and/or data to change at least one parameter controlling pressure swing adsorption cycle of the respiratory care device.

The data communicated from the computing-based device 110 and/or the application 120 may be received through a communication module 151 of the controller 152 of the respiratory care device 150. The controller 152 can cause the operation parameters of the respiratory care device 150 to be changed according to the data communicated from the computing-based device 110 and/or the application 120, and the changed parameters are then used to control the operation of the respiratory care device 150 accordingly (e.g., by generating appropriate control signals based, among other things, on the changed values of the operation parameters). Subsequently, the respiratory care device may operate for a period of time (which may be a pre-determined period of time) according to the changed operation parameters, during which time data about the operation of the respiratory care device 150 resulting from the change to the operation parameters is collected by the device 150 (for example, at the memory devices 153 coupled to the controller 152). The respiratory care device 150 then communicates to the computing-based device 110 resultant data representative of operation of the respiratory care device 150 resulting from the controllable change to the one or more operation parameters. The technician can then view the resultant data which may further facilitate identifying and remedying the problem(s) associated with the respiratory care device.

In some embodiments, changing operation parameters, in the manner described above, may also be performed for medical or therapeutic purposes. For example, a physician, a respiratory technician, or other qualified clinician may be able to set operational attributes of a respiratory care device by making changes to operation parameters using an interface provided at a remote computing-based device accessed by the clinician. Such an interface may be similar, for example, to the interface 710 depicted in FIGS. 7-12. Changes to operation parameters may be based, under those circumstances, on the communicated data relating to the current operation of the respiratory care device and/or medical data representative of the user's medical/physical attributes and conditions (e.g., the user's breathing rate, oxygen level in the user's blood, heart rate, temperature, etc.) Data representative of the changes to one or more operation parameters is then communicated to the respiratory care device in the manner described herein.

The respiratory care device 150 depicted in FIG. 1, which communicates data relating to the operability of the device to the computing-based device 110 and/or the application 120, may be one of, for example, a supplemental oxygen device (such as an oxygen concentrator or a device that fills gas cylinders) which may include a liquid oxygen storage module, a ventilator, a continuous positive airway pressure ("CPAP") device, etc.

By way of example only, in some embodiments, the respiratory care device 150 may be an oxygen concentrator, such as the Eclipse® device developed and manufactured by SeQual Technologies Inc. A description of an oxygen concentrator is provided for example, in U.S. patent application Ser. No. 12/553,801, entitled "System and Method for Controlling Bolus Pulse Duration Based on Inspiratory Time in an Oxygen Concentration System," the content of which is hereby incorporated by reference in its entirety. Briefly, and with reference to FIG. 2A, a portable oxygen concentration device 200, is shown. The oxygen concentration device 200 includes an air separation device 202, such as an oxygen gas generator, that separates concentrated oxygen gas from ambient air, an energy source such as rechargeable battery, battery pack, or fuel cell 204 that powers at least a portion of the oxygen gas generator 202, one or more optional output sensors 206 used to sense one or more conditions (e.g., medical attributes) of a user 208, the environment, etc., to determine the oxygen output needed by the user or required from the device 200. The device 200 also includes a control unit 210 which may be linked to the output sensor 206, the air separation device 202, and the energy source 204 to control the operation of the air separation device 202. As described herein, in some embodiments, changes to operation parameters of the oxygen concentration device 200 (and/or other respiratory care devices) may be based on operation parameters of the device 200 communicated to an external computing-based device (such as the device 110 depicted in FIG. 1) and/or on data representative of the user 208's medical attributes as may have been determined and collected by the one or more output sensors 206. The data collected by the one or more output sensors 206 may then be communicated to an external computing-based device such as the computing based device 110 of FIG. 1.

Operational characteristics of the oxygen concentrator device 200, such as flow rate, oxygen concentration level, etc., may also be based, in some embodiments, on controllable operation parameters that can be set or programmed by the user, a technician, etc. As described herein, such operation parameters may be controlled remotely from, for example, the computing-based device 110 of FIG. 1 using the interfacing application 120. Control data communicated from the computing-based device 110 and/or the application 120 may be received by a communication module coupled to the control unit 210. The control unit 210 may be implemented as a processor-based device, data and instructions, controllers, or other electrical circuit elements for controlling and managing the system. The device 200 may include a user interface 154 to communicate with the control unit 210. The user interface 154 may have a configuration resembling the control interface 710 depicted in the screenshots of FIGS. 7-12. The interface 154 enables the user, provider, clinician, technician etc., to enter data, e.g., prescription oxygen level, flow rate, etc., to control the operation of the device 200.

Figure 2A:
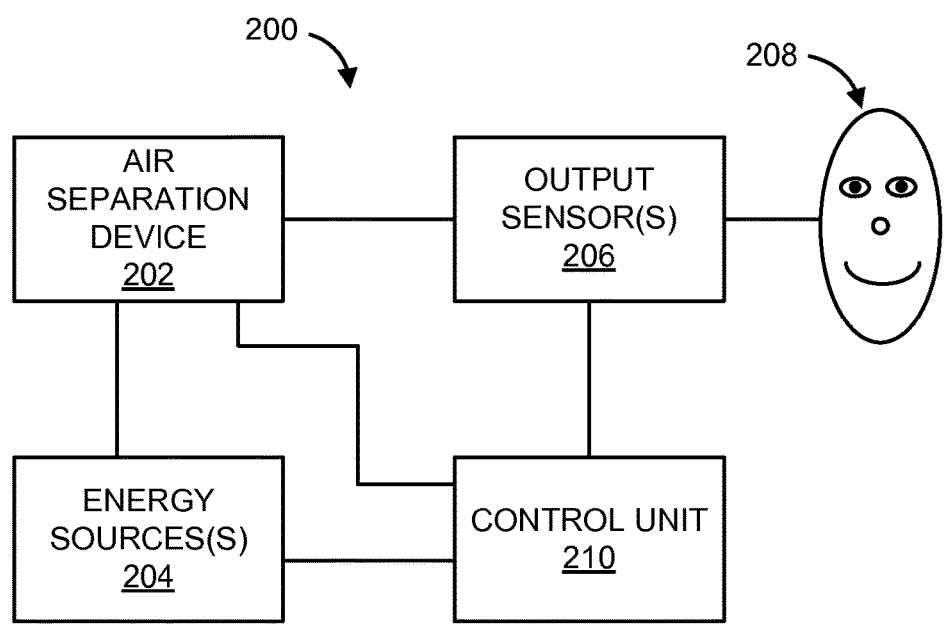
FIGS. 2A and 2B are schematic diagrams of an example oxygen concentrator device.
Figure 2B:
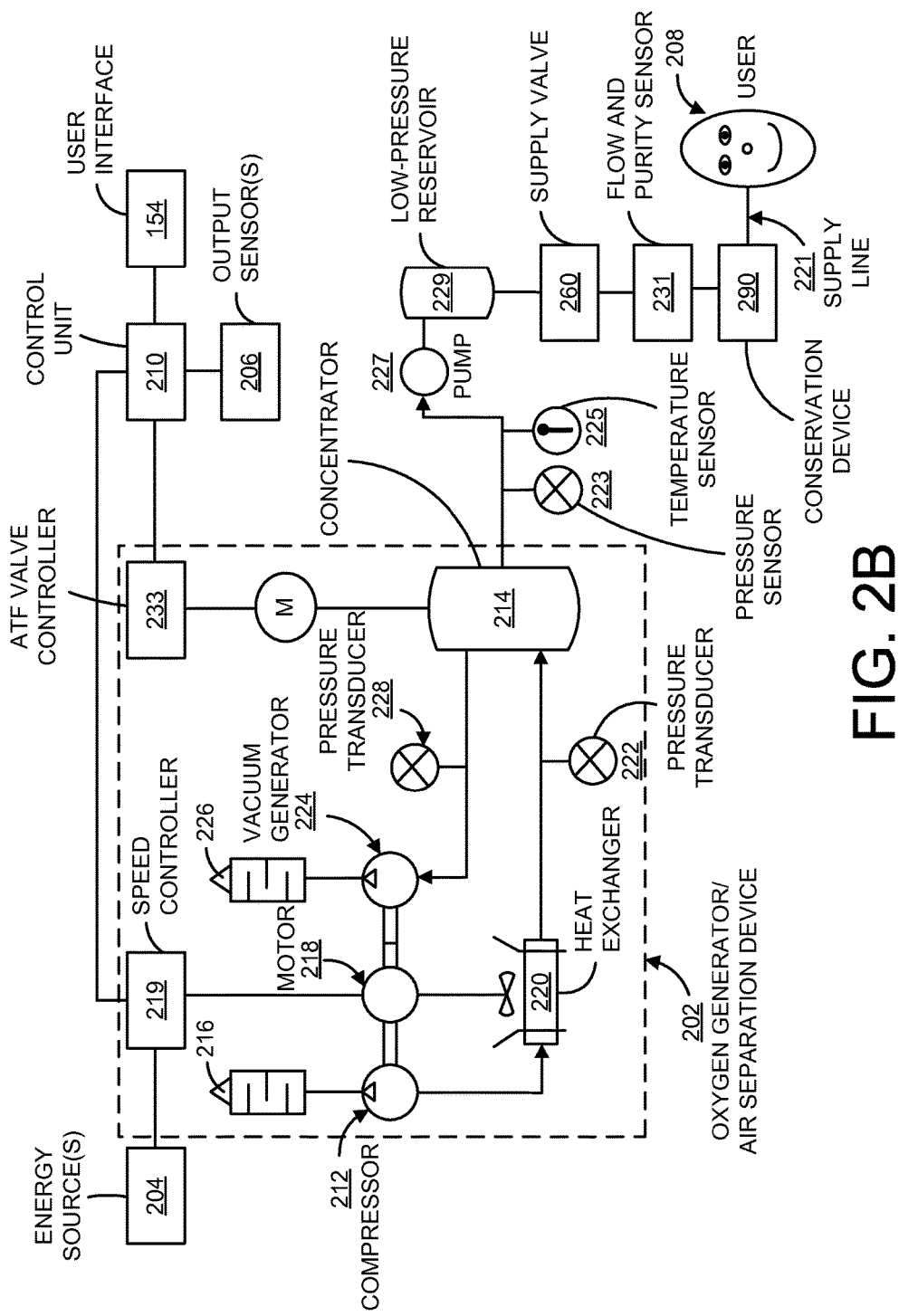

With reference to FIG. 2B, showing a more detailed schematic diagram of the device 200 of FIG. 2A, in some embodiments, the air separation device may be an oxygen generator 202 that generally includes a pump such as a compressor 212 and an oxygen concentrator 214 (OC), which may be integrated. The concentrator 214 may be configured to separate oxygen from air, and may also be configured, in some implementations, to perform air separation to produce nitrogen, purified hydrogen, remove water from air, etc. Ambient air may be drawn through an inlet muffler 216 by the compressor 212. The compressor 212 may be driven by one or more DC motors 218 that may be powered by a DC electrical current supplied by the rechargeable battery 204 or may be driven by an external AC or DC power source. The motor 218 may also drive the cooling fan part of the heat exchanger 220. A variable-speed controller (also referred to as VSC) or compressor motor speed controller 219 may be integral with or separate from the control unit 210. The compressor 212 delivers the air under pressure to the concentrator 214. In some embodiments, air is delivered to the concentrator 214 at 7.3 psig nominal and may range from 5.3 to 12.1 psig. At maximum speed, the flow rate of feed may have a minimum of 23.8 SLPM at inlet conditions of 14.696 psi absolute, 70 degrees F. 50% relative humidity.

Compressor technologies that may be used for the compressor 212 include, for example, rotary vane, linear piston with wrist pin, linear piston without wrist pins, mutating discs, scroll, rolling pistons, diaphragm pumps, etc. In some embodiments, the compressor 212 and vacuum generator 224 are integrated with the motor 218. In some embodiments, the compressor 212 may operate at a 3:1 speed ratio, with a low speed of at least 1,000 rpm and a 15,000 hour operating life when run at full speed. Operating temperature surrounding the compressor/motor system may be 32 to 122 degrees F. Storage temperature may be −4 to 140 degree F. A shaft mounted fan or blower may be incorporated with the compressor 212 for compressor cooling and optionally complete system cooling.

The variable-speed controller 219 enables reducing the power consumption requirements of the compressor 212. Using a variable-speed controller, the speed of the compressor 212 may be varied based on the activity level of the user, metabolic condition of the user, environmental conditions, and/or other conditions indicative of the varying oxygen needs of the user as may be determined, for example, through the one or more output sensors 206.

The heat exchanger 220 may be located between the compressor 212 and the concentrator 214 to cool or heat the air to a desired temperature before entering the concentrator 214. A filter (not shown) may be located between the compressor 212 and the concentrator 214 to remove any impurities from the supply air, and a pressure transducer 222 may be located between the compressor 212 and the concentrator 214 to get a pressure reading of the air flow entering the concentrator 214.

The concentrator 214 separates oxygen gas from air for eventual delivery to the user 208. The concentrator 214 connects to the user 208 via a supply line 221 which may include one or more of, for example, a pressure sensor 223, a temperature sensor 225, a pump 227, a low-pressure reservoir 229, a supply valve 260, a flow and purity sensor 231, and a conservation device 290. These various components constituting the supply line 221 may be coupled using tubes, connectors, etc. The pump 227 may be driven by a motor. The oxygen may be stored in the low-pressure reservoir 229 and delivered to the user 208. The supply valve 260 may be used to control the delivery of oxygen gas from the low-pressure reservoir 229 to the user 208 at atmospheric pressure.

In some implementations, the concentrator 214 may also be configured to dispel exhaust gas. In some embodiments, a vacuum generator 224, which may also be driven by the motor 218 and integrated with the compressor 212, draws exhaust gas from the concentrator 214 to improve the recovery and productivity of the concentrator 214. The exhaust gas may exit the device 200 through an exhaust muffler 226. A pressure transducer 228 may be located between the concentrator 214 and the vacuum generator 224 to get a pressure reading of the exhaust flow from the concentrator 214.

In some embodiments, the concentrator 214 may be an Advanced Technology Fractionator (ATF) that may be used for medical and industrial applications. The ATF may implement a pressure swing adsorption (PSA) process, a vacuum pressure swing adsorption (VPSA) process, a rapid PSA process, a very rapid PSA process or some other process. If a PSA or VPSA process is implemented, the concentrator may include a rotating valve or a non-rotating valve mechanism to control air flow through multiple sieve beds. The sieve beds may be tapered so that they have larger diameter where gaseous flow enters the beds and a smaller diameter where gaseous flow exits the beds. Suitable sieve materials that may be used in the ATF concentrator 214 include LithiumX Zeolite that allows for a high exchange of Lithium ions. Other types of concentrators or air-separation devices, including membrane separation types and electrochemical cells (hot or cold), may also be used.

An ATF valve controller 233 may be integral with or separate from the control unit 210 and may be coupled, via a device M (for example, a motor), with valve electronics in the concentrator 214 for controlling the valve(s) of the concentrator 214.

Figure 3A:
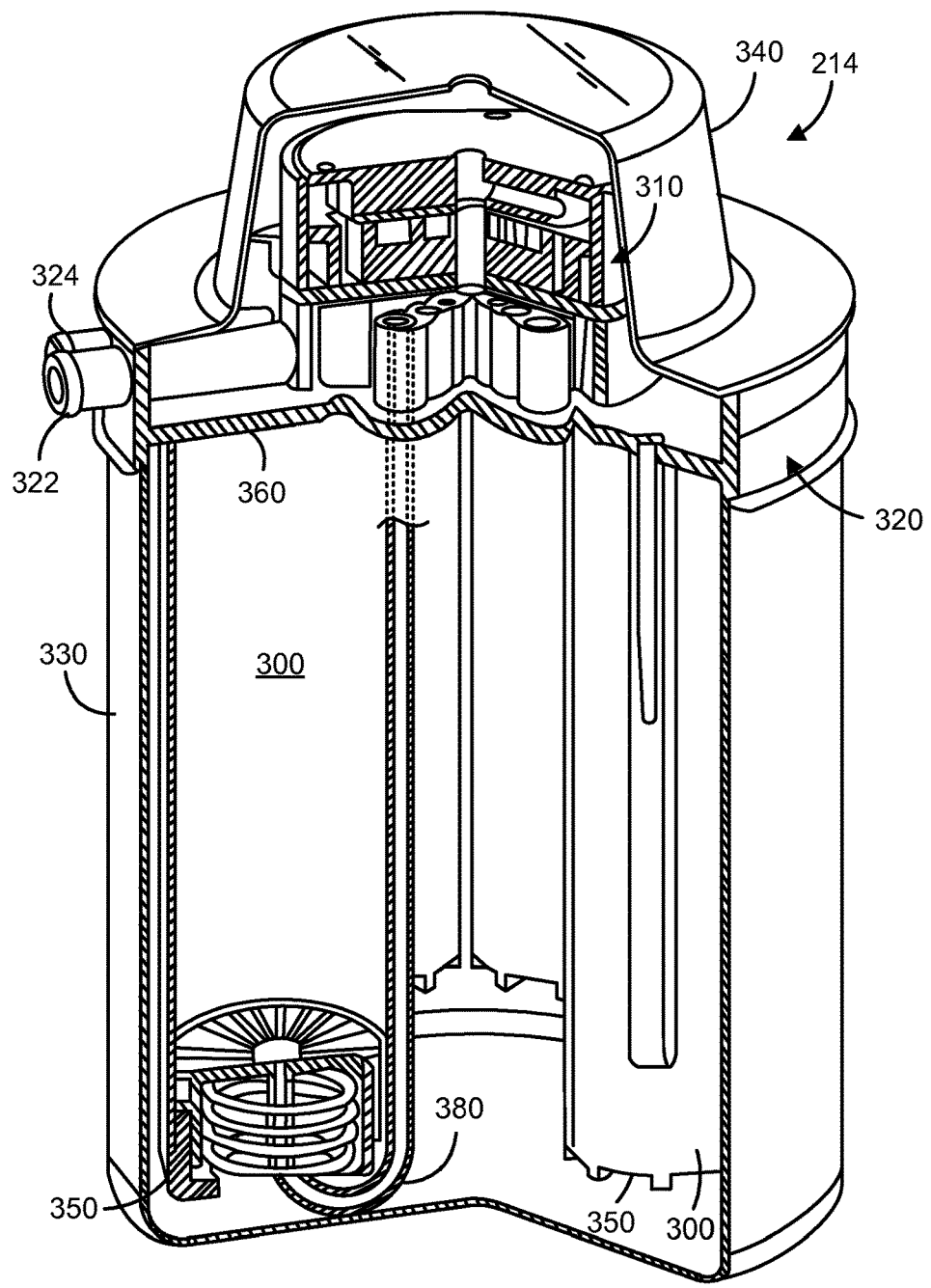
FIGS. 3A and 3B are a cutout and exploded views of an example concentrator that may be used in an oxygen generator such as the oxygen generator of the oxygen concentrator device shown in FIGS. 2A and B.
Figure 3B:
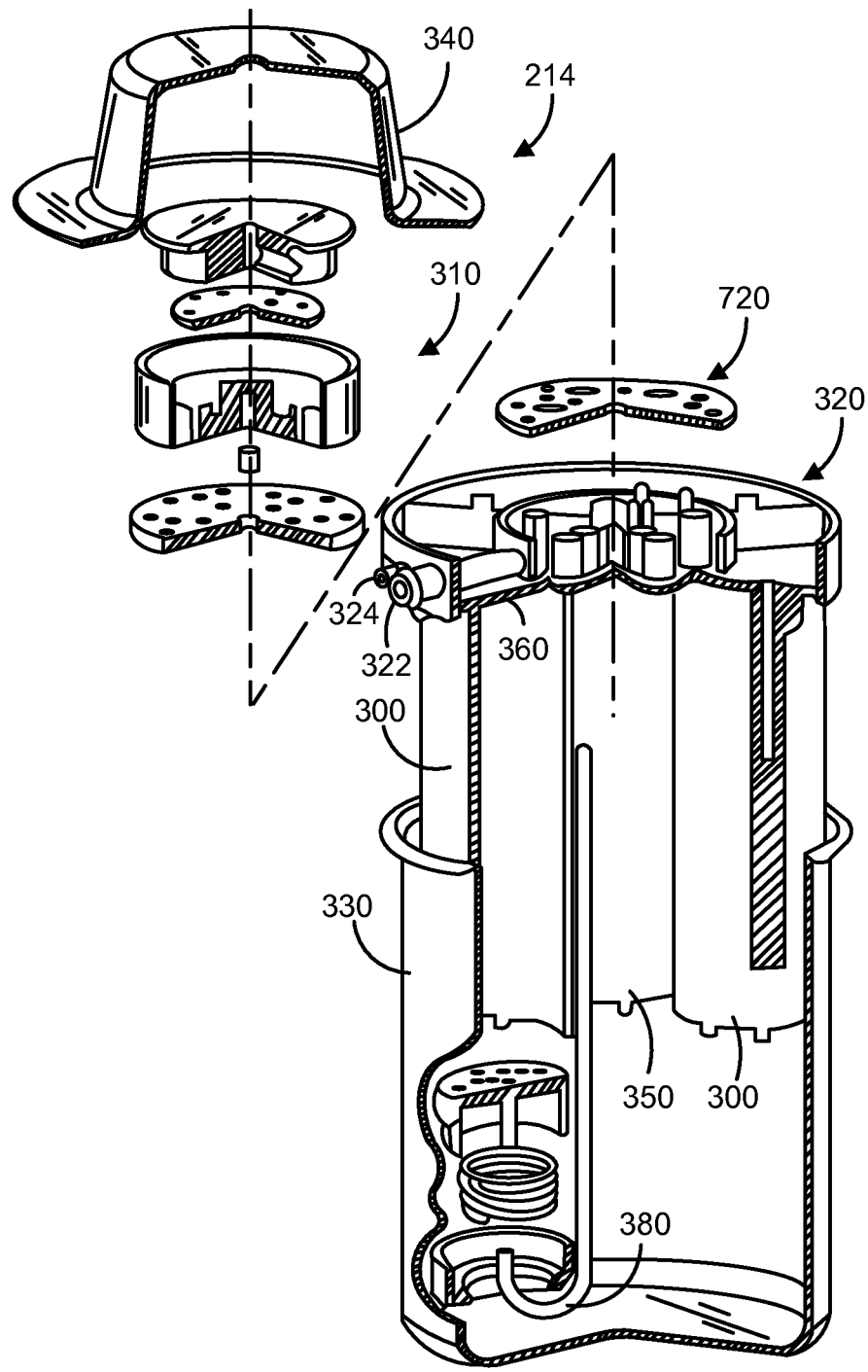

FIGS. 3A and 3B are a cutout and exploded views of an example concentrator 214 that may be used in an oxygen generator such as the oxygen generator 202 shown in FIGS. 2A and B. As shown, the concentrator 214 includes five adsorption beds 300, each containing a bed of adsorbent material which is selective for a particular molecular species of fluid (liquid or gas) or contaminant, a rotary valve assembly 310 for selectively transferring fluids through the adsorption beds 300, an integrated tube-assembly and a manifold 320, a product tank cover 330, and a valve assembly enclosure 340. In some embodiments, the adsorption beds 300 are molded plastic vessels surrounded by the product tank cover 330, which may be made of metal (e.g., aluminum).

Each adsorption bed 300 includes a product end 350 and a feed end 360. The product ends 350 of the beds 300 communicate with incoming product passages (not shown) of the manifold 320 through product lines 380 for communication with the rotary valve assembly 310. The manifold 320 may also include outgoing product passages that communicate the rotary valve assembly 310 with the interior of the product tank 330, an incoming feed passage that communicates the rotary valve assembly 310 with a feed pressure line 322, and a vacuum chamber that communicates the rotary valve assembly 310 with a vacuum pressure line. A product delivery line 324 (which may be similar to the supply line 221 described with respect to FIG. 2B) communicates with the interior of the product tank 330. A vacuum pressure line may communicate directly or indirectly with the vacuum generator 224 for drawing exhaust gas from the concentrator 214.

In operation, air flows from the compressor 212 to the feed pressure line 322, through the incoming feed passage of the manifold 320. From there, air flows to the rotary valve assembly 310 where it is distributed back through outgoing feed passages of the manifold 320. From there, the feed air flows to the feed ends 360 of the adsorption beds 300. The adsorption beds 300 include adsorbent media that is appropriate for the species that will be adsorbed. For oxygen concentration, a packed particulate adsorbent material that adsorbs nitrogen relative to oxygen in the feed air may be used so that oxygen is produced as the non-adsorbed product gas. An adsorbent such as a highly Lithium exchanged X-type Zeolite may be used. A layered adsorbent bed that contains two or more distinct adsorbent materials may also be used. As an example, for oxygen concentration, a layer of activated alumina or silica gel used for water adsorption may be placed near the feed end 360 of the adsorbent beds 300 with a lithium exchanged X-type zeolite used as the majority of the bed toward the product end 350 to adsorb nitrogen.

The resulting product oxygen gas flows towards the products ends 350 of the adsorption beds 300, through the product lines 380, through incoming product passages of the manifold 320, and to the rotary valve assembly 310, where it is distributed back through the manifold 320 via the outgoing product passage and into the product tank 330. From the product tank 330, oxygen gas is supplied to the user through the product delivery line 324 and/or the supply line 221.

Figure 4:
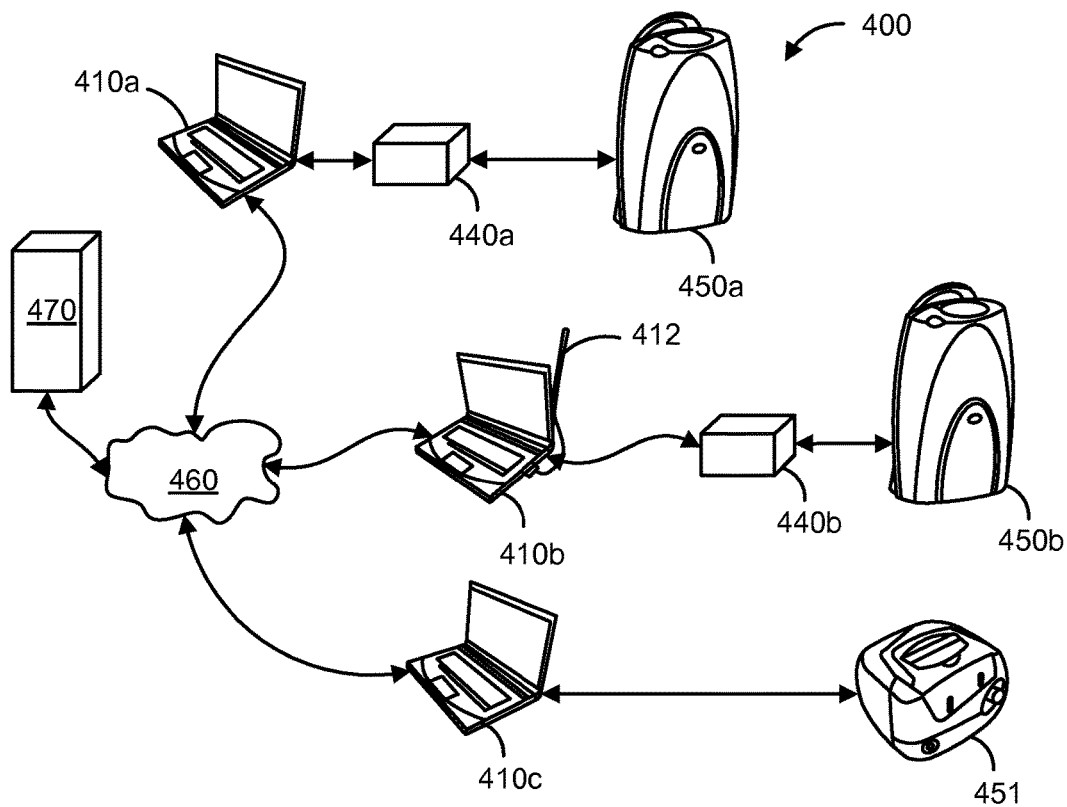
FIG. 4 is a schematic diagram of another example embodiment of a system for diagnosing, updating, and repairing home medical oxygen concentrators.

With reference now to FIG. 4, another example embodiment of a system 400 for operating (diagnosing, updating, repairing, setting operation parameters, etc.) a respiratory care device (e.g., a home medical oxygen concentrator such as the one depicted in FIGS. 2 and 3) is shown. The system 400 includes multiple respiratory care devices, which, in the example of FIG. 4, includes two oxygen concentrators 450*a* and *b*, and a CPAP device 451. The types and number of respiratory care devices shown in FIG. 4 is for illustration purposes only. Any number of respiratory care devices, and additional types of respiratory care devices (e.g., ventilators)

may be used. General configuration of the system 400 and its general functionality is similar to the configuration and functionality of the system 100, except that system 400 is shown to include multiple respiratory care devices and multiple computing-based devices configured to communicate with various respiratory care devices through communication links (wireless or wire-based) that, like the system 100, may or may not require an interfacing device (a modem, a communication gateway or adapter—such as 440a, 440b) to establish a communication link between the various communication based devices and the various respiratory care devices to which they are coupled.

For example, as shown, a computing-based device 410b communicate wirelessly with a respiratory care device 450b which may not have a wireless communication module (e.g., a wireless transceiver). Accordingly, in that situation, the computing-based device 450b communicates wirelessly (via an antenna 412) with an intermediate wireless communication device 440b (e.g., a communication modem or adapter) that has a wire-based connection to the communication module of the respiratory care device 150 (the physical connection may be from an input/output port of the modem 440b, to an input/output port of respiratory care device 450b), through which data and control instructions are received and then processed by, for example, a controller which may be similar to the controller 152 shown in FIG. 1. In another example, the respiratory care device 451 communicates (in this case, via a physical connection) without using an intermediate communication modem or adapter.

The system 400 enables the various computing-based devices, which are external to the respiratory care devices and may be remote or local computing-based devices, to also establish communication links between each other via, for example, a network 460 (which may be a private or public network, and may be packet-based network or a network based on other technologies). Thus, for example, a field technician accessing a respiratory care device in one location (e.g., respiratory care device 450a), may seek help from another technician, located at some remote location near another respiratory care device (e.g., device 451). The two respective computing-based device 410a and 410c may thus communicate data to each other. For example, the computing-based device 410a can communicate the data it received from the respiratory care device 450a to the computing-based device 410c, whereupon the received data can be presented on an interface that is part of an application, such as the application 120 in FIG. 1, and may include one or more system software modules that run on the computing-based device 410c. The technician at the computing-based device 410c can review the data to attempt to identify and resolve the problem (with for example, a troubleshooting guide such as the guide 130 of FIG. 1), and may further change certain operation parameters that are then communicated to the respiratory care device 450a via the computing-based device 410a. In some implementations, the software module(s) may include one or more functions. One function includes the ability to remotely examine a data log for the particular respiratory care device. Elements of the data log include, but are not limited to, compressor temperature, flow rate, bolus size, and ambient pressure. Another function includes the ability to remotely start/stop the respiratory care device (e.g., oxygen concentrator), change flow settings and mode, adjust compressor and ATF speed, etc.

In some embodiments, the system 400 may also include a remote server 470 (e.g., located at a service center) where generally skilled technicians may be located. Accordingly, data relating to the operation of the various respiratory care device deployed in FIG. 1 may be communicated to the server 470 (directly, or via intermediate computing-based devices) whereupon the technician(s) can review the data (presented on an interface such as those shown in FIGS. 7-12), perform diagnosis, make adjustments to the operation parameters of the particular respiratory care device, make changes to operation parameters so as to review the operational response of the respiratory care device resulting from the changes, provides verbal instructions to the patients or technician on how to remedy any problems, etc. Where the technician makes adjustments/changes to operation parameters, the data representative of those adjustments/changes is communicated back to the particular respiratory care device.

In some implementations, the system 100 of FIG. 1 and the system 400 of FIG. 4 may be enabled by using software keys stored, for example, on removable memory devices (e.g., USB memory stick, SD card, other memory device). Particularly, in some embodiments, one or more software modules required for operation of the system 100 or the system 400, such as software modules of the interface application (such as the application 120) to control the operation of the respiratory care device, may be installed from a removable memory device, or may be activated (e.g., if the software modules are already installed on the host computing-based device or are running from the removable memory devices) only if a particular software key (e.g., some alphanumerical string) is found on the removable memory device, and that key matches, or is otherwise consistent, with an expected value of the key. In some implementations, the removable memory devices may include one or more software modules that launch and run if the software key is installed at the local host computing-based device.

The one or more software modules automatically attempt to connect the local computing-based device (e.g., the device 110 in FIG. 1) with the serial ports. Thus, in some embodiments, upon activation of the interfacing application, the application checks if the ports are setup correctly. If the ports are not setup correctly, the one or more software modules display a dialog that helps users to connect with the particular respiratory care device. Upon connection with the respiratory care device, the one or more software modules may automatically detect the firmware part number, version and other information of the respiratory care device 150, and upgrades the new firmware if required and selected.

As noted, an interfacing application, implemented using the one or more software modules, may continuously or periodically monitor and display all the information from the connected respiratory care device, and may enable users to calibrate and configure the respiratory care devices. The one or more software modules continuously or periodically cause all the data of the connected respiratory care device to be transferred to the external computing-based device.

In some embodiments, a procedure to prevent operation of the application 120 (and thus prevent operations that may be performed by the systems 100 or 400 as described herein) includes embedding a key code in a file allocation table (FAT) within a memory device. Generally, content stored in memory devices can be accessed via a type of table of contents. Disk Drives, RAM disks, memory sticks, and other types of memory devices are configured to update the information and access files using such a table of contents. Information specific to a memory device is also stored and used to identify bad memory areas and other data necessary to function. Standardized implementations to manage content stored on memory devices include the File Allocation Table (FAT) implementation (e.g., FAT12, FAT16, FAT32, VFAT), the New Technology File System (NTFS) implementations, etc.

For a memory device that uses FAT to manage and perform access control, when the memory device is copied, the FAT table is not generally copied. Generally, special procedures/applications are required to view and/or modify the FAT table. Users typically are not required or expected to alter a FAT table. The systems and methods described herein (including implementations of interfacing applications, such as the interfacing application 120, an example of which is SeQual Technologies' EDAT application) can take advantage of this fact to store a key into the FAT table. When, for example, an interfacing application is launched, the key stored in the FAT is examined and, if valid, the application is enabled for operation.

An upgrade (e.g., software upgrade of a respiratory care device such as an oxygen concentrator like SeQual Technologies' Eclipse® oxygen concentrator) can be performed, for example, by storing an upgrade key in the FAT table (or in other types of memory areas reserved for memory device management and control). For example, the number of upgrades may be written to a FAT table. After an upgrade is made, an application, such as an interfacing application (e.g., EDAT) decrements that number. This controls the number of upgrades a single key allows. An advantage of placing a key and number of upgrades in the FAT table is that if the memory device is copied, the FAT table generally is not copied with it, so that copying a memory device in order to attempt an unauthorized use of an interfacing application will generally not include the keys necessary to enable operation of the copied applications. Additionally, when a memory device is reformatted, the key or number of upgrades is lost.

Thus, in some implementations, the FAT may specify the number of software upgrades that may be implemented into a respiratory care device. Embedding a key code in the FAT can prevent copying of the system memory device that is necessary for the system application to function because the copying of memory content generally does not result in the copying of the FAT. Because the software key may be embedded to the FAT, the software key will therefore not be copied along with the content of the memory device. If the number representative of the software upgrade times is also embedded into the FAT, this too can be effective to prevent unauthorized copying and/or use of the software modules necessary for operation of the systems 100 or 400. Because generally only authorized personnel will have legitimate copies of memory devices with legitimate software keys, this procedure can also provide better quality control for servicing the respiratory care devices because only trained personnel will generally be provided with memory devices with authorized copies of the modules needed to enable the interfacing application.

Figure 5:
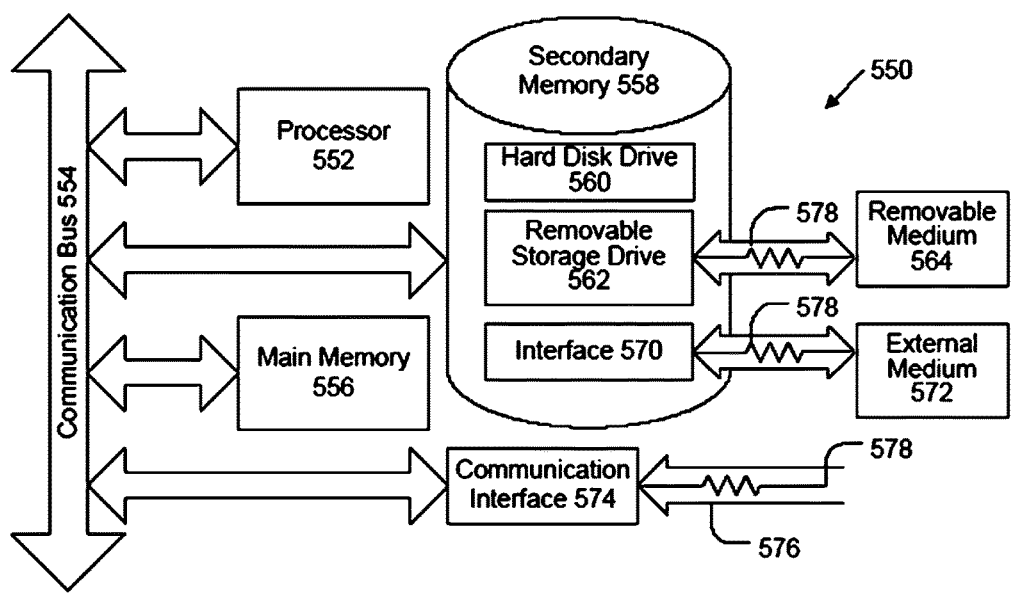
FIG. 5 is a block diagram of an example computer system that may be used to implement the various computing and processor-based devices described herein.

FIG. 5 is a block diagram illustrating an example computer system 550 that may be used to implement the various computing and processor-based devices described herein. For example, the computer system 550 may be used in conjunction with the respiratory care device 150 (e.g., the controller 152 of the device 150), the computing-based devices 410 a-c, the remote computing-based devices 470, etc. However, other computer systems and/or architectures may be used.

The computer system 550 preferably includes one or more processors, such as processor 552. Additional processors may be provided, such as an auxiliary processor to manage input/output, an auxiliary processor to perform floating point mathematical operations, a special-purpose microprocessor having an architecture suitable for fast execution of signal processing algorithms (e.g., digital signal processor), a slave processor subordinate to the main processing system (e.g., back-end processor), an additional microprocessor or controller for dual or multiple processor systems, or a coprocessor. Such auxiliary processors may be discrete processors or may be integrated with the processor 552.

The processor 552 may be connected to a communication bus 554. The communication bus 554 may include a data channel for facilitating information transfer between storage and other peripheral components of the computer system 550. The communication bus 554 further may provide a set of signals used for communication with the processor 552, including a data bus, address bus, and control bus (not shown). The communication bus 554 may comprise any standard or non-standard bus architecture such as, for example, bus architectures compliant with industry standard architecture ("ISA"), extended industry standard architecture ("EISA"), Micro Channel Architecture ("MCA"), peripheral component interconnect ("PCI") local bus, or standards promulgated by the Institute of Electrical and Electronics Engineers ("IEEE") including IEEE 488 general-purpose interface bus ("GPIB"), IEEE 696/S-100, and the like.

Computer system 550 may also include a main memory 556 and may also include a secondary memory 558. The main memory 556 provides storage of instructions and data for programs executing on the processor 552. The main memory 556 is typically semiconductor-based memory such as dynamic random access memory ("DRAM") and/or static random access memory ("SRAM"). Other semiconductor-based memory types include, for example, synchronous dynamic random access memory ("SDRAM"), Rambus dynamic random access memory ("RDRAM"), ferroelectric random access memory ("FRAM"), and the like, including read only memory ("ROM").

The secondary memory 558 may optionally include a hard disk drive 560 and/or a removable storage drive 562, for example a floppy disk drive, a magnetic tape drive, a compact disc ("CD") drive, a digital versatile disc ("DVD") drive, etc. The removable storage drive 562 reads from and/or writes to a removable storage medium 564. Removable storage medium 564 may be, for example, a floppy disk, magnetic tape, CD, DVD, etc.

The removable storage medium 564 may be a non-transitory computer readable medium having stored thereon computer executable code (e.g., software) and/or data. The computer software or data stored on the removable storage medium 564 is read into the computer system 550 as electrical communication signals 578.

In alternative embodiments, secondary memory 558 may include other similar implementations for enabling computer programs or other data or instructions to be loaded into the computer system 550. Such implementations may include, for example, an external storage medium 572 and an interface 570. Examples of external storage medium 572 may include an external hard disk drive or an external optical drive, or and external magneto-optical drive.

Other examples of secondary memory 558 may include semiconductor-based memory such as programmable read-only memory ("PROM"), erasable programmable read-only memory ("EPROM"), electrically erasable read-only memory ("EEPROM"), or flash memory (block oriented memory similar to EEPROM). Also included are any other removable storage units 572 and interfaces 570, which allow software and data to be transferred from the removable storage unit 572 to the computer system 550.

Computer system 550 may also include a communication interface 574. The communication interface 574 allows software and data to be transferred between computer system 550 and external devices (e.g. printers), networks, or information sources. For example, computer software or executable code may be transferred to computer system 550 from a network server via communication interface 574. Examples of communication interface 574 include a modem, a network interface card ("NIC"), a communications port, a PCMCIA slot and card, an infrared interface, and an IEEE 1394 fire-wire, just to name a few, which enable wire-based or wireless communication.

Communication interface 574 preferably implements industry promulgated protocol standards, such as Ethernet IEEE 802 standards, Fiber Channel, digital subscriber line ("DSL"), asynchronous digital subscriber line ("ADSL"), frame relay, asynchronous transfer mode ("ATM"), integrated digital services network ("ISDN"), personal communications services ("PCS"), transmission control protocol/Internet protocol ("TCP/IP"), serial line Internet protocol/point to point protocol ("SLIP/PPP"), and so on, but may also implement customized or non-standard interface protocols as well.

Software and data transferred via communication interface 574 are generally in the form of electrical communication signals 578. These signals 578 may be provided to communication interface 574 via a communication channel 576. Communication channel 576 carries signals 578 and can be implemented using a variety of wired or wireless communication means including wire or cable, fiber optics, conventional phone line, cellular phone link, wireless data communication link, radio frequency ("RE") link, or infrared link, just to name a few.

Computer executable code (i.e., computer programs or software) may be stored in the main memory 556 and/or the secondary memory 558. Computer programs can also be received via communication interface 574 and stored in the main memory 556 and/or the secondary memory 558. Such computer programs, when executed, enable the computer system 550 to perform the various functions described herein.

In this disclosure, the term "computer readable medium" is used to refer to any non-transitory media used to provide computer executable code (e.g., software and computer programs) to the computer system 550. Examples of these media include main memory 556, secondary memory 558 (including hard disk drive 560, removable storage medium 564, and external storage medium 572), and any peripheral device communicatively coupled with communication interface 574 (including a network information server or other network device). These computer readable media are means for providing executable code, programming instructions, and software to the computer system 550.

In embodiments that are implemented using software, the software may be stored on a computer readable medium and loaded into computer system 550 by way of removable storage drive 562, interface 570, or communication interface 574. In such embodiments, the software is loaded into the computer system 550 in the form of electrical communication signals 578. The software, when executed by the processor 552, causes the processor 552 to perform the features and functions described herein.

Various embodiments may also be implemented primarily in hardware using, for example, components such as application specific integrated circuits ("ASICs"), or field programmable gate arrays ("FPGAs"). Implementation of a hardware state machine capable of performing the functions described herein may also be used. Various embodiments may also be implemented using a combination of both hardware and software.

Figure 6:
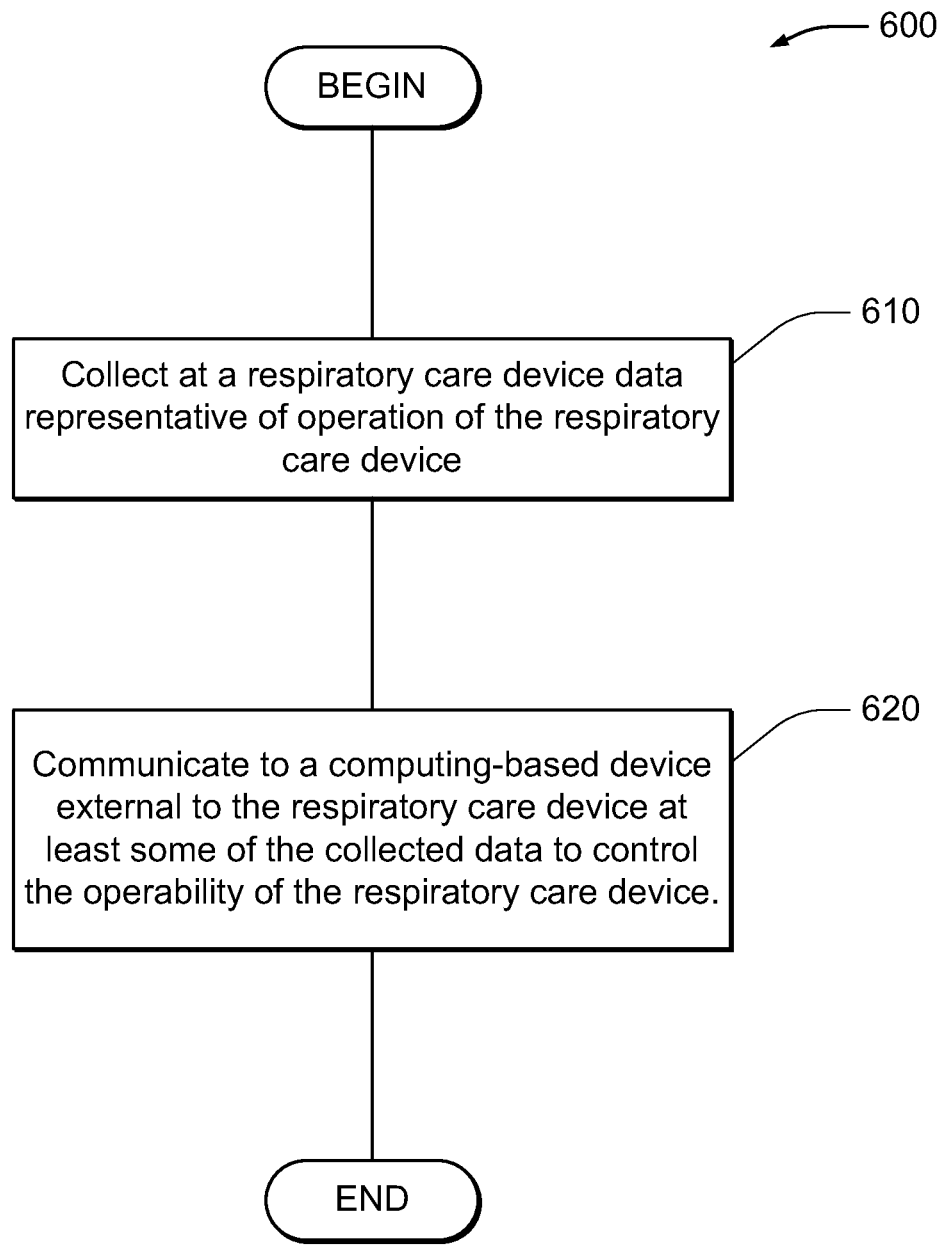
FIG. 6 is a flowchart of an example procedure to operate a respiratory care device (e.g., remotely diagnose and repair a respiratory care device, remotely set operation parameters for such devices, etc.).

With reference now to FIG. 6, a flowchart of an example procedure 600 for operating a respiratory care device is shown. To perform various operations on the respiratory care device (troubleshooting, manipulating operational attributes of the device, remote setting of operation parameters for therapeutic reasons), data representative of operation of the respiratory care device is collected 610 at a respiratory care device. The data may be collected at one or more memory devices of the respiratory device, which may be housed within the respiratory case device, or may be external to the respiratory care device. Such memory devices are typically in communication with the controller of the respiratory care devices. The data collected may include data providing measures about the performance of the devices, historical operational data (e.g., operational events), medical/monitoring data regarding the patient who is using the respiratory care device, etc.

At least some of the data representative of the operation of the respiratory care device (which may include medical data of the patient using the device) is communicated 620 to a computing-based device (such as the device 110 depicted in FIG. 1) that is external to the respiratory care device to control the operability of the respiratory care device. The communicated data may be used to enable identifying problems with the respiratory care device, to alter operation parameters (so as to glean further insight as to any underlying problems from the resultant data), to subsequently set new values for operation parameters of the respiratory care device (e.g., motor speed, oxygen concentrator, etc.) for medical/therapeutic reasons, etc.

Figure 7:
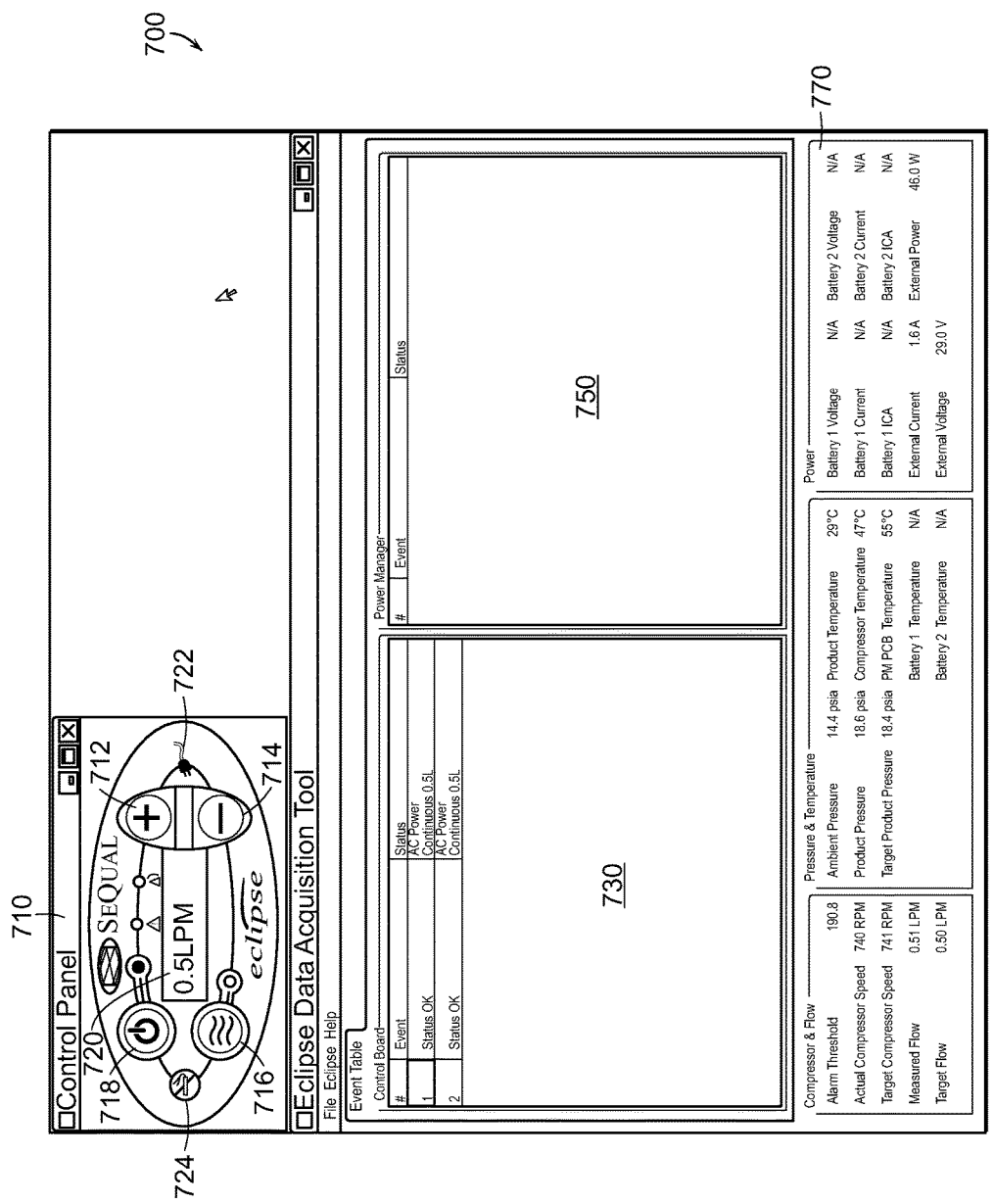
FIGS. 7-12 are screenshots of an example interface that may be used to operate/control (e.g., from an external computing-based device) operability of a respiratory care device.

Screenshots shown in FIGS. 7-12 provide illustrative examples of operations of the systems, methods, products and implementations described herein. The screenshots of FIGS. 7-12 illustrate an interface to control and manage an oxygen concentrator. However, similar interfaces can be used for other types of respiratory care devices. FIG. 7 is a screenshot of a graphical interface 700 to provide a user data representative of operational attributes and behavior of a respiratory care device. The illustrated graphical interface may be implemented using, for example, an application such as the application 120 of FIG. 1 executing on a computing-based device such as the device 110 of FIG. 1. The graphical interface 700 includes a control panel area 710 to provide a graphical representation of the user interface located on the respiratory care device. In the embodiments of FIGS. 7-12, the control panel area 710 is a graphical representation similar to the actual interface appearing on an Eclipse® oxygen concentrator. Accordingly, a user operating the interface 700 can interact with the graphical representation of the interface in the control panel 710 in a similar manner to the way the user would interact directly with the interface of the oxygen concentrator. This simplifies the remote interaction with the respiratory care device because the graphical representation of the interface will have the use and feel of the actual interface of the physical respiratory care device.

The interface represented in the control panel area 710 includes a controllable power button 718 to enable powering the oxygen concentrator on and off. Thus, when a communication link is established between the computing device running an interfacing application (be it a computing device at a remote location or at a location proximate to the physical oxygen concentrator), selecting the power button 718 will communicate to the physical oxygen concentrator data and/or control signals that upon being received by the oxygen concentrator (via the device's communication module) will be processed by the oxygen concentrator's controller to cause the device to power on or off. The control panel area also includes an air flow mode button 716 that controls whether air flow is provided in continuous or pulse mode, and a "+" and "−" buttons 712 and 714 to enable controlling the values appearing in the value screen area (e.g., to increment or decrement the particular parameter being displayed). The control panel also includes a so-called hidden button 724 (represented as a "do not smoke" icon that serves as a warning to unqualified users not to attempt to manipulate that button). The hidden button enables qualified personnel to access various menus through which various parameters of the respiratory care device can be retrieved and/or altered. These parameters values correspond to parameters that the patient and other unqualified users should not attempt to modify.

The interface 700 further includes an event table control board area 730 providing a report from the oxygen concentrator's control section (e.g., status information), an event table power manager area 750 providing a report from the oxygen concentrator's power section, and a parameter value area 770 providing data (e.g., real time data) about the values and operations of various components of the oxygen concentrator. Accordingly, upon establishing a communication link between the interfacing application running on the computing-based device (as noted herein, in some embodiments, such a connection will be enabled and allowed to be established only if a removable memory device required for operation of the application includes a requisite software key), the computing-based device receives data from the oxygen concentrator representative of the operation of the oxygen concentrator, and uses that data to populate the various areas of the interface 700. As shown in FIG. 7, the screen area 720 of the control panel 710 displays the current air flow of the oxygen concentrator as being 0.5 LPM (liters per minute). The interface's event table area 730 provides information indicating that the oxygen concentrator is connected to AC power (also indicated by the AC plug icon 722 in the control panel area 710), and further indicates that air flow is in continuous mode. The power manager section 750 of the event table does not include any information at the present time. The parameter area 770 provides various parameter values regarding the compressor and flow operation of the oxygen concentrator including compressor speed, alarm threshold (which is generally set to twice the allowed oxygen concentration), etc., pressure and temperature information, and power information. The power section of the parameter value area 770 indicates that no information is available regarding the battery power (battery parameter values are represented as "N/A") indicating that there is a potential problem with the batteries of the oxygen concentrator.

Figure 8:
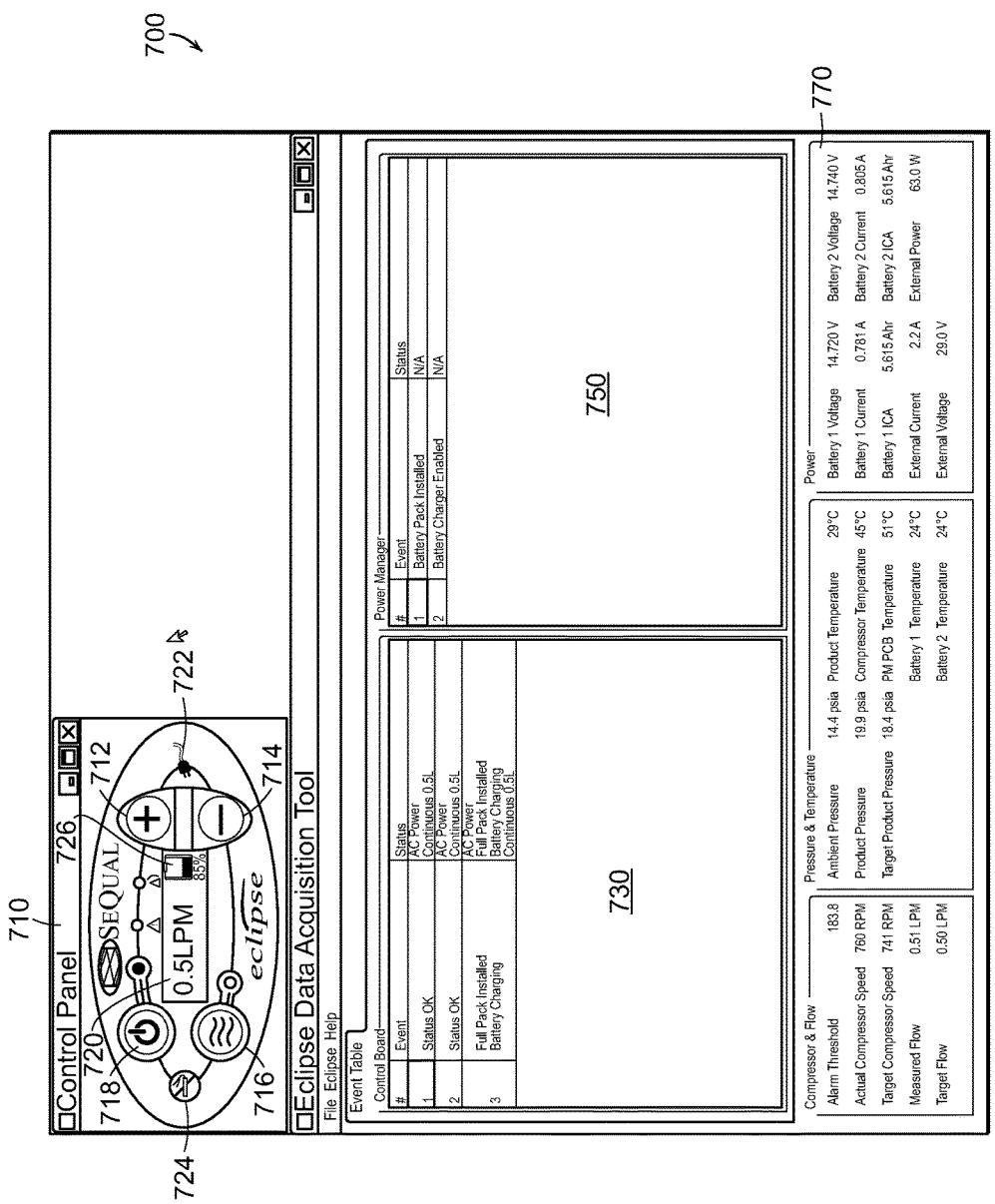

FIG. 8 is a screenshot of the interface 700 of FIG. 7 at a later time instance after one or more additional operations have been completed subsequent to what was reported in the screenshot shown in FIG. 7. As shown, following the indication in FIG. 7 that battery power information was not available, a trained user was able to determine, based on that information, and with or without the use of troubleshooting guide, that there is a problem with the battery. Particularly, the presentation of that information led the user (technician) to determine that the battery of the oxygen concentrator is not connected, and to therefore remedy the problem by connecting the battery (which may have been done by a field technician him/herself determining and remedying the problem, or by a field technician acting pursuant to instructions from a remotely located technician). After the battery is connected, a battery icon 726 is presented in the control panel area 710, along with a graphical representation that the battery is now charging (since the oxygen concentrator is also connected to an AC power source that can charge the battery), as represented by a "water fall" effect in which the bars inside the battery icon fill up and empty out. Also represented below the battery icon is the charge level (e.g., 85%) of the battery. The connection of the battery to the oxygen concentrator is also reflected in an update of the power manager area 750 of the event table which reports, in FIG. 8, that battery pack was installed and enabled. Similarly, the control board area 730 of the event table section likewise shows that the battery pack was installed and enabled. The parameter area 770 presents information regarding the now connected battery pack, including, for example, the battery's voltage and current.

Figure 9:
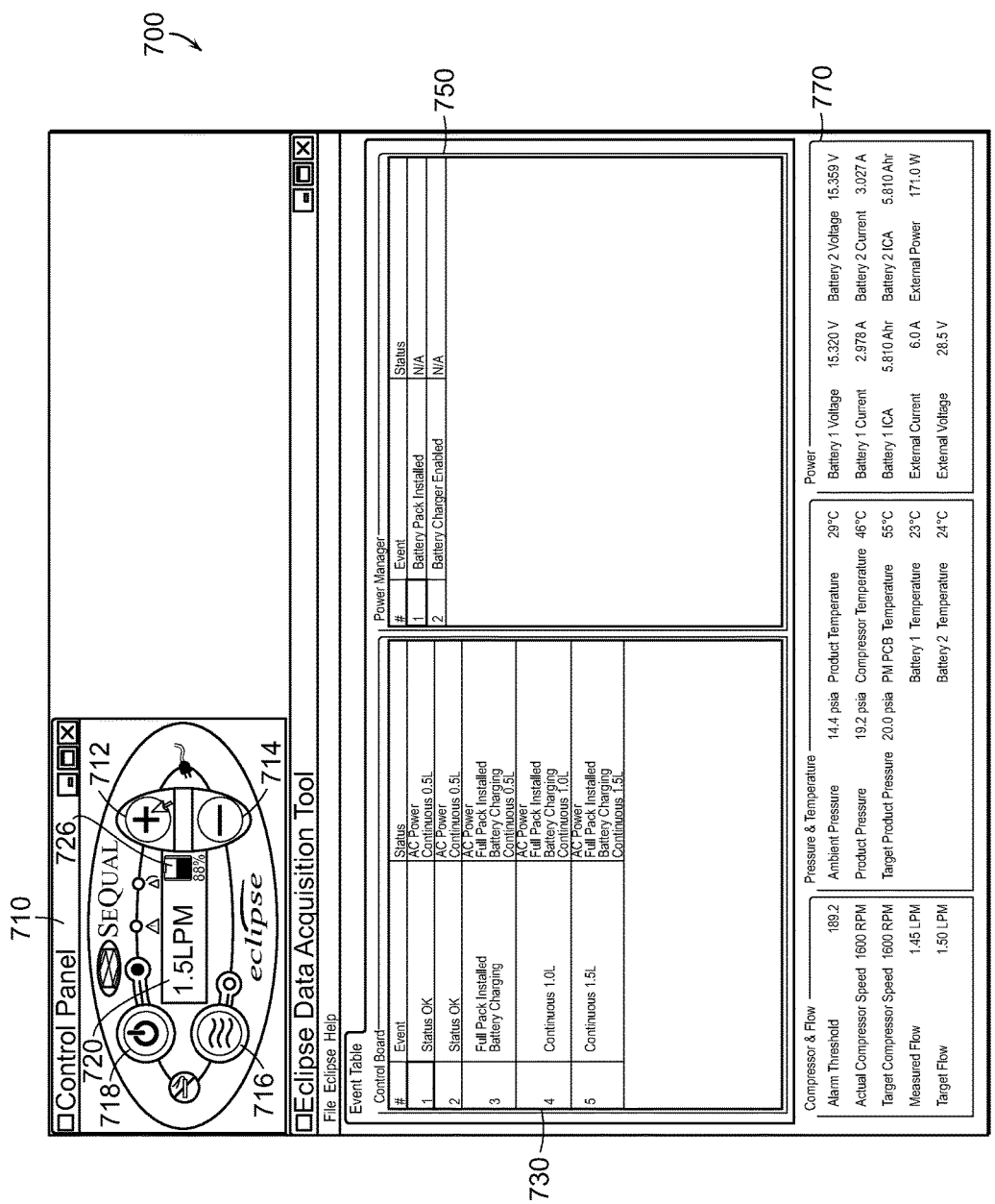

FIG. 9 is a screenshot of the interface 700 of FIGS. 7-8 at a later time instance after one or more operations have been completed subsequent to what was reported in the screenshot shown in FIG. 8. As shown in the screenshot of FIG. 9, the user interacting with the oxygen concentrator decides to increase the flow to 1.5 LPM (e.g., to see how that change affects the operation of the oxygen concentrator, to set the new value for clinical/therapeutic reasons, etc.) Adjustment of the flow parameters is achieved by selecting (e.g., clicking on) the "+" button 712 to set the desired value. In some embodiments, the flow parameter value indicated in the screen area 720 may be incremented by increments of 0.5 LPM. Thus, as shown in control board area 730 of the event table, the oxygen concentrator recorded two events relating to the adjustment of the flow parameter, namely the event in which the value increased from 0.5 LPM to 1.0 LPM, and the event in which the value increased from 1.0 LPM to 1.5 LPM. The change of the flow parameter also causes a change to the compressor speed, which increased from its 760 RPM speed in FIG. 8 to 1600 RPM in FIG. 9. The oxygen concentrator and/or the interfacing application also compute the target or expected compressor speed as a way to verify conformity between actual values and target values. In FIG. 9, the compressor's actual speed and target speed are in agreement. However, had there been a discrepancy between those values, this could have informed a technician of a potential problem. Also shown in FIG. 9 is an indication the charging battery is now at a charge level of 88%.

Figure 10:
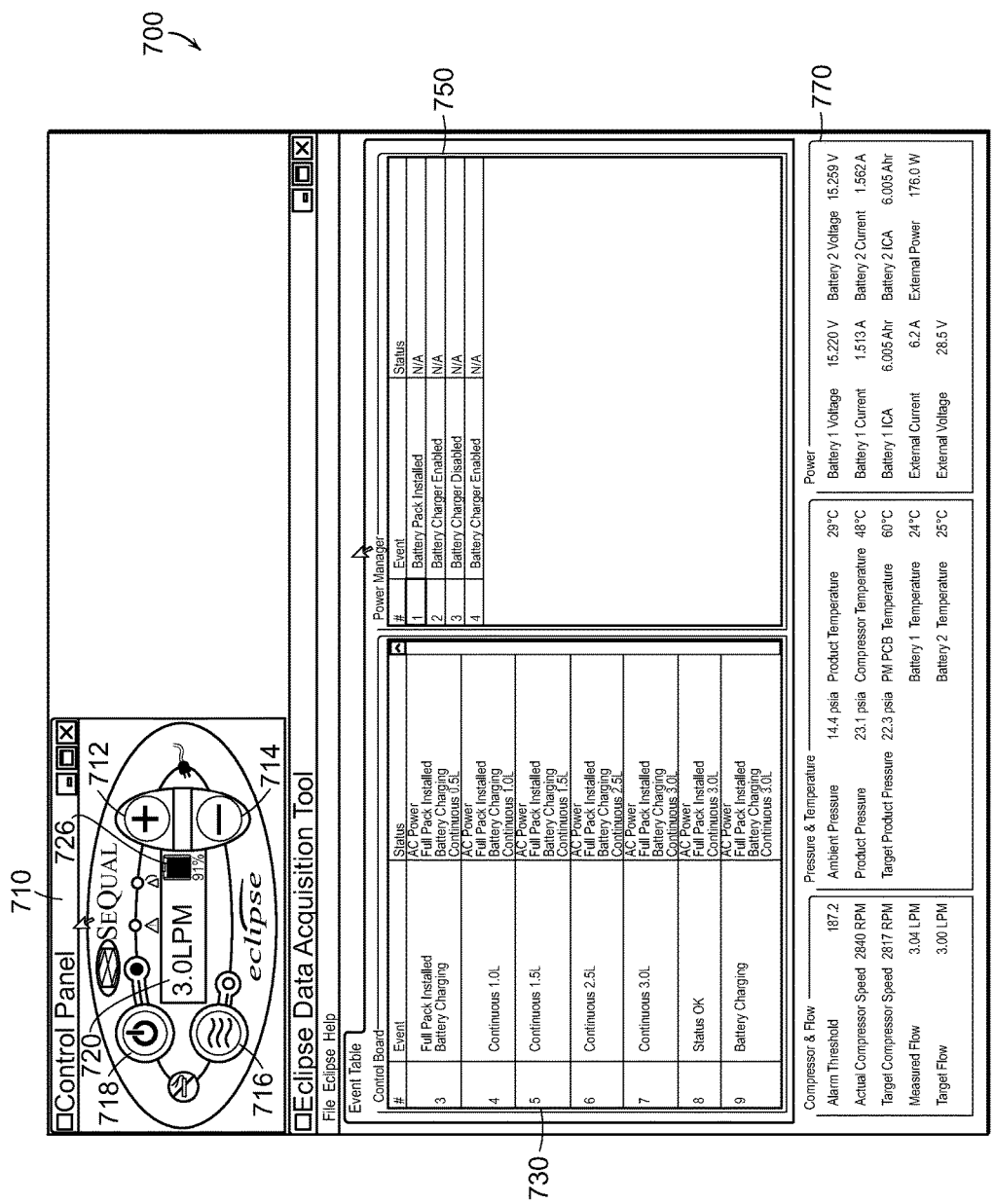

FIG. 10 is a screenshot of the interface 700 of FIGS. 7-9 at a later time instance after one or more additional operations have been completed subsequent to what was reported in the screenshot shown in FIG. 9. As shown in the screenshot of FIG. 10, the user interacting with the oxygen concentrator decides to increase the flow to 3 LPM. Adjustment of the flow parameters is achieved by selecting the "+" button 712 to set the desired value. As shown in the control board area 730 of the event table, the oxygen concentrator recorded two events relating to the adjustment of the flow parameter, namely, the event in which the value increased from 1.5 LPM to 2.5 LPM, and the event in which the value increased from 2.5 LPM to 3.0 LPM. The change of the flow parameter also causes a change to the compressor speed, which increases to 2840 RPM in FIG. 10 (which is in approximate agreement with the target compressor speed of 2817). Also shown in FIG. 10 is an indication the charging battery is now at a charge level of 91%. The power manager section of the event table also shows that during the period between the time instance of FIG. 9 and the time instance of FIG. 10, the battery pack went off then came on again. The fact that the battery pack came on again may indicate to the technician interacting with the oxygen concentrator that the oxygen concentrator likely does not have any significant power problem because if it did (e.g., the battery became too hot or otherwise became disabled) the charging battery would not have come back on.

Figure 11:
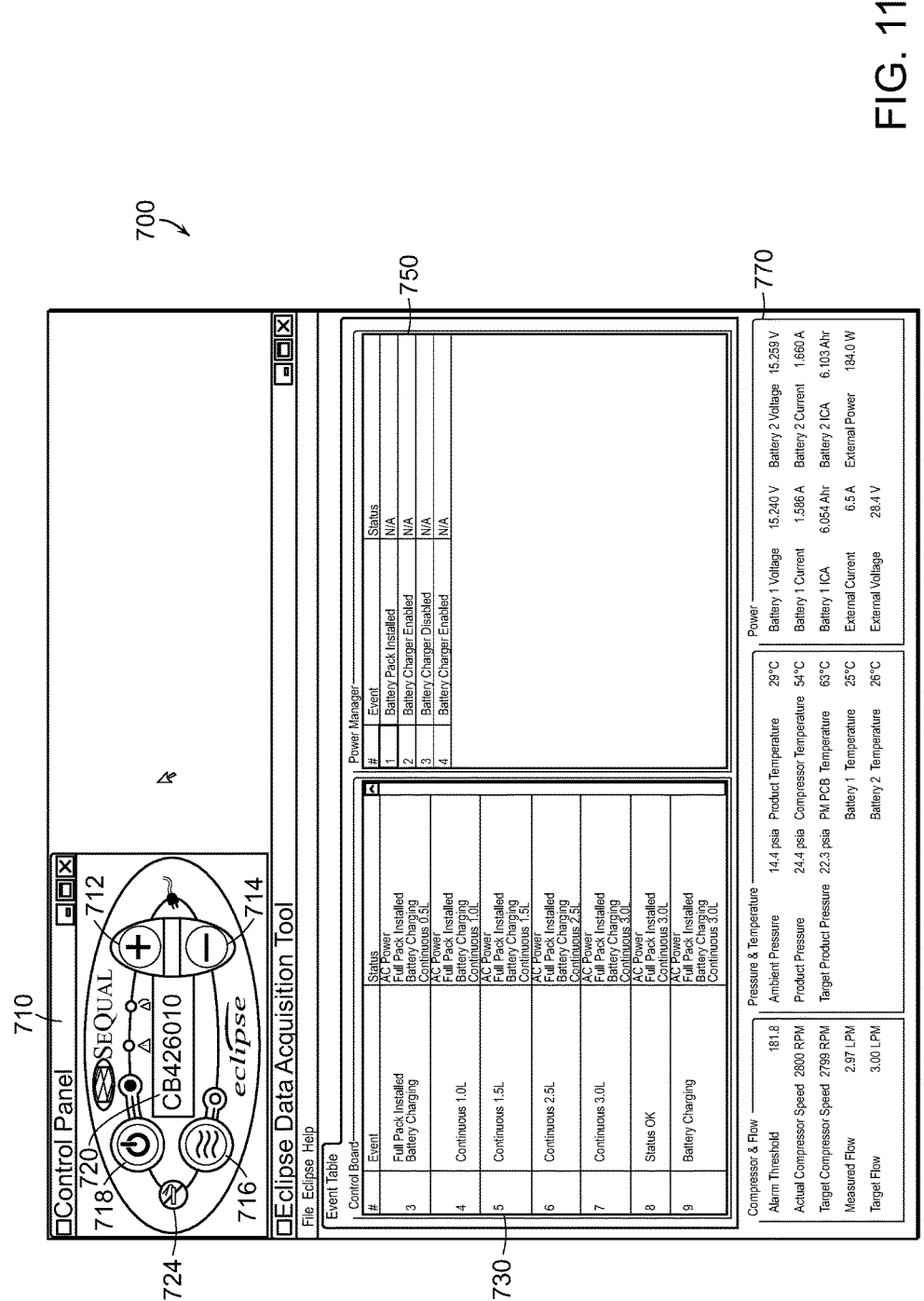

Continuing now with FIG. 11, a screenshot of the interface 700 of FIGS. 7-10 at a later time instance after one or more additional operations have been completed subsequent to what was reported in the screenshot shown in FIG. 10 is shown. FIG. 11 illustrates operation enabled through the "hidden" button 724. As noted, a user may select the hidden button to access various screens, menus and/or parameter values, such as screens to change the alarm code, adjust pulse sensitivity, set bolus values, etc. In FIG. 11, through manipulation of the hidden button, the user obtains information about the control board used in the particular oxygen concentrator. As shown in the screen area 720 of the control panel area 710, the interfacing application retrieves and presents to the user information that the control board is part 4260 and is revision 1.0. If the indicated version was an old version, the interfacing application could have been used to load up the new version.

Figure 12:
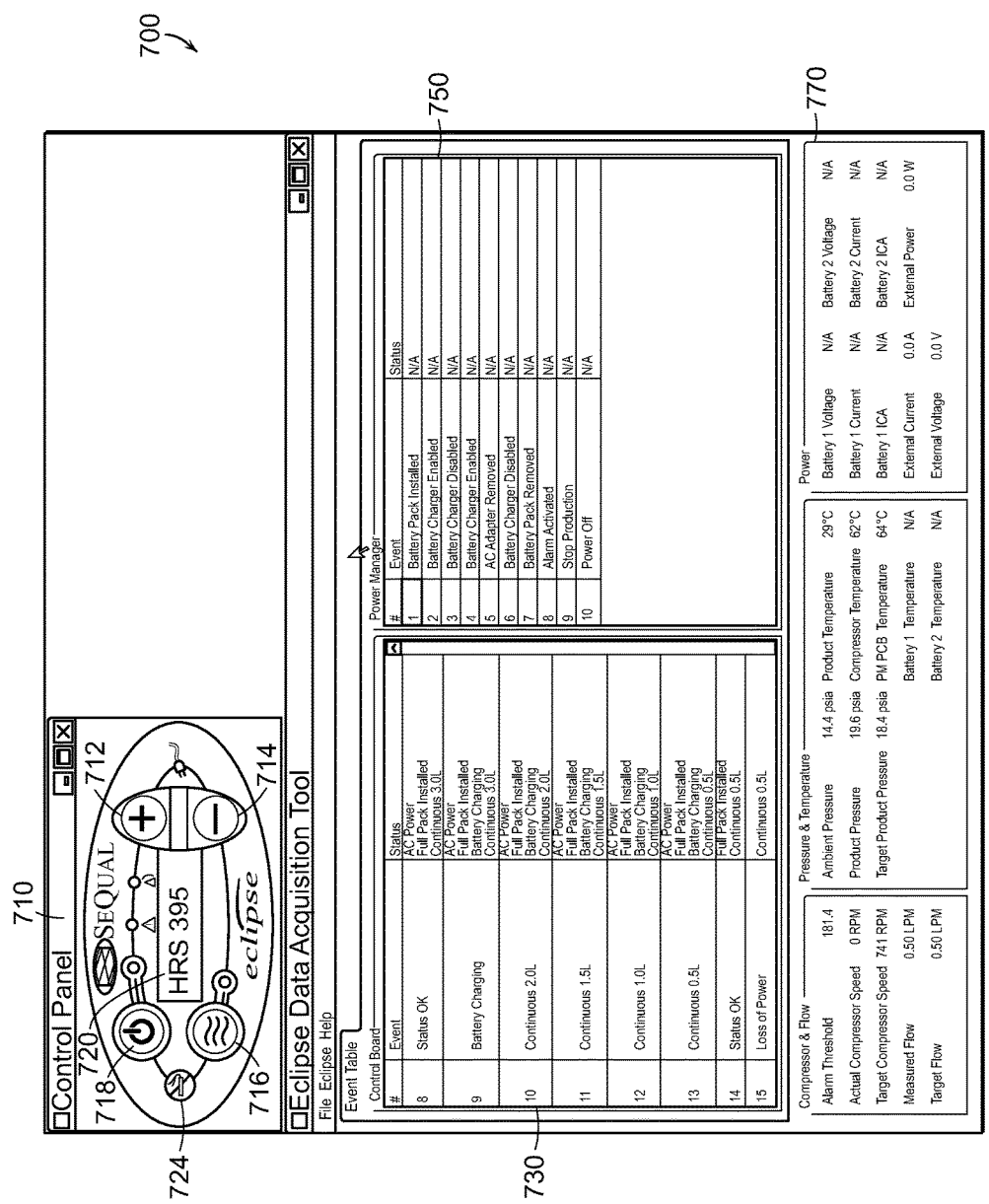

With reference now to FIG. 12, a screenshot of the interface 700 of FIGS. 7-11 at a later time instance after one or more additional operations have been completed subsequent to what was reported in the screenshot shown in FIG. 11 is shown. FIG. 12 illustrates another operation enabled through the "hidden" button 724. Particularly, through manipulation of the hidden button, the user obtains information about the number of hours the system has been on (e.g., 395 hours). The screenshot of FIG. 12 also shows that during the period between the time instance of FIG. 11 and the time instance of FIG. 12, the flow value was reduced from 3.0 LPM to 0.5 LPM (as reported in the control board area 730 of the event table of the interface 700), and that subsequent to that power was lost (as indicated in item 15 of the control board area 730, item 5 of the power manager area 750 of the event table, and in the change off color of the power plug icon 722 of the control panel area 710). Additional events that are reported in the power manager section 750 include the disabling and removal of the battery (also indicated in the power section of the parameter area 770), the fact that the alarm was activated, that production stopped, and that power was turned off.

Accordingly, as illustrated in FIGS. 7-12 a user interacting with a respiratory care device through an interface such as the interface 700 implemented through an interfacing application can obtain detailed information about operations and various constituents of the respiratory care device (and may also obtain clinical information about the user), and is able to control, also through the interface, the operation of the respiratory care device based, at least in part, on the received data.

The various illustrative logical blocks, modules, circuits, and methods described in connection with the above described figures and the embodiments disclosed herein can often be implemented as electronic hardware, computer software, or combinations of both.

Moreover, the various illustrative logical blocks, modules, and methods described in connection with the embodiments disclosed herein can be implemented or performed with a general purpose processor, a digital signal processor ("DSP"), an ASIC, FPGA or other programmable logic device, discrete gate or transistor logic, discrete hardware components, or any combination thereof designed to perform the functions described herein. A general-purpose processor can be a microprocessor, but in the alternative, the processor can be any processor, controller, microcontroller, or state machine. A processor can also be implemented as a combination of computing devices, for example, a combination of a DSP and a microprocessor, a plurality of microprocessors, one or more microprocessors in conjunction with a DSP core, or any other such configuration.

Additionally, the methods/procedures described in connection with the embodiments disclosed herein can be embodied directly in hardware, in a software module executed by a processor, or in a combination of the two. A software module can reside in RAM memory, flash memory, ROM memory, EPROM memory, EEPROM memory, registers, hard disk, a removable disk, a CD-ROM, or any other form of storage medium including a network storage medium. An exemplary storage medium can be coupled to the processor such that the processor can read information from, and write information to, the storage medium. In the alternative, the storage medium can be integral to the processor. The processor and the storage medium can also reside in an ASIC.

A number of implementations of the invention have been described. Nevertheless, it will be understood that various modifications may be made without departing from the spirit and scope of the invention. Accordingly, other embodiments are within the scope of the following claims.

What is claimed is:

1. A method for operating respiratory care devices, the method comprising:

collecting, at a respiratory care device comprising a compressor and a vacuum generator that are powered by a same motor, data representative of operation of the respiratory care device, the respiratory care device providing a respiratory gas to a patient, the collected data comprising oxygen concentration level values, measured oxygen flow, and oxygen product pressure, the compressor configured to convert ambient air to compressed air, the respiratory care device further comprising an oxygen concentrator configured to receive the compressed air from the compressor to separate the compressed air into oxygen and exhaust gases, the vacuum generator configured to receive and vacuum out the exhaust gases, wherein the collected data is specifically representative of the oxygen concentrator;

communicating, to a computing-based device wirelessly connected to the respiratory care device via a communication network, at least some of the collected data to control operability of at least one of the compressor, the vacuum generator, and the oxygen concentrator, the computing-based device comprising a graphical user interface that displays a control board area including a first event table providing a report of a control section of the respiratory care device including a first event table event listing for each event identifying the event and a corresponding status, where the first event table event listings are arranged in chronological order, a power manager area including a second event table providing a report of an electrical power section of the respiratory care device including a second event table event listing for each event identifying the event and a corresponding status, where the second event table event listings are arranged in chronological order, and a parameter value area showing real-time data of a plurality of components of the respiratory care device;

automatically communicating model data to the computing-based device, the model data being representative of a part number of the respiratory care device;

communicating to the computing-based a graphical representation of an actual, physical user interface of the respiratory care device, the graphical representation including multiple graphical representations of buttons of the actual, physical user interface of the respiratory care device arranged in a spatial configuration that is a replica of the actual, physical user interface of the respiratory care device such that the graphical representation of an actual, physical user interface of the respiratory care device is displayed on a common page along with the first and second event tables and the parameter value area, with the control board area on the computing-based device wirelessly connected to the respiratory care device and the control board data is updated in real time to reflect any changes to the control board data based on interaction with the graphical representation of the actual, physical user interface of the respiratory care device;

connecting a user locally to the respiratory care device, with the user:
i) determining, at the respiratory care device, that a problem associated with the respiratory care device cannot be corrected at the respiratory care device; and
ii) transferring control of the respiratory care device to the computing-based device wirelessly connected to the respiratory care device as a result of determining, at the respiratory care device, that a problem associated with the respiratory care device cannot be corrected at the respiratory care device.

2. The method of claim 1, wherein the respiratory care device is one of: a supplemental oxygen device, a ventilator, and a continuous positive air pressure (CPAP) device.

3. The method of claim 2, wherein the supplemental oxygen device comprises a storage of liquid oxygen.

4. The method of claim 1, wherein the communicating of the at least some collected data enables a determination of one or more problems relating to the operability of the respiratory care device.

5. The method of claim 4, wherein the one or more problems relating to the operability of the respiratory care device are determined based on the communicated at least some of the collected data.

6. The method of claim 1, wherein the communicating of the at least some collected data enables a determination of clinical modification of operation parameters to change a clinical performance of the respiratory care device.

7. The method of claim 1, further comprising:
communicating, to the respiratory care device, data to controllably change one or more operation parameters of the respiratory care device to cause a change in the operability of at least one of the compressor, the vacuum generator, and the oxygen concentrator;
changing the one or more operation parameters of the respiratory care device according to the communicated data to controllably change the one or more operation parameters; and
communicating, to the external computing-based device, resultant data representative of operation of the respiratory care device resulting from the controllable change to the one or more operation parameters.

8. The method of claim 7, wherein communicating to the respiratory care device data to controllably change the one or more operation parameters comprises communicating data to change at least one parameter controlling flow setting of the respiratory care device, data to change at least one parameter controlling a pressure swing adsorption cycle of the oxygen concentrator, and one or more of:
data to change at least one parameter controlling the start and stop operation of the respiratory care device, data to change at least one parameter controlling a compressor mode of the compressor, and data to change at least one parameter controlling bolus frequency of the respiratory care device.

9. The method of claim 1, wherein the collected data comprises one or more of: event tables, real time data, real time and historical data records, firmware revisions, number of operating hours, compressor speed of the compressor, target oxygen flow, ambient pressure, target oxygen product pressure, battery temperature, oxygen temperature, compressor temperature associated with the compressor, electronics printed circuit board temperature, battery voltage, battery capacity, alarm threshold, electrical voltage from an external source, electrical current provided from the external source, and power provided by the external source.

10. The method of claim 1, wherein the communicating of at least some of the collected data comprises:
determining if at least one removable memory device storing data used to enable the computing-based device to communicate with the respiratory care device includes a software key stored in a file allocation table of the at least one removable memory device; and
preventing at least some of communication operations between the computing-based device and respiratory care device if the file allocation table of the at least one removable memory device does not include the software key, and enabling the communication operations between the computing-based device and the respiratory care device if the file allocation table of the at least one removable memory device includes the software key.

11. The method of claim 1, further comprising:
storing, at a file allocation table of at least one removable memory device, a value indicative of upgrades allowed for one or more of software components implemented on the computing-based device, and one or more software components implemented on the respiratory care device; and
decrementing the stored value indicative of the allowed upgrades when a software upgrade is performed for one of: the one or more software components implemented on the computing-based device, and the one or more software components implemented on the respiratory care device.

12. The method of claim 1, further comprising:
providing the communicated at least some of the collected data to a troubleshooting guide, the troubleshooting guide applying the provided data to determine one or more problems relating to the operability of the respiratory care device.

13. The method of claim 1, further comprising:
collecting medical data relating to a user of the respiratory care device;
communicating the medical data relating to the user to the computing-based device external to the respiratory care device; and
determining values of the operation parameters controlling operation of the respiratory care device based on at least a part of the communicated data relating to the operation of the respiratory care device and the medical data.

14. The method of claim 13, wherein the medical data comprises an oxygen level in blood of the user, a temperature of the user, and one or more of: a breathing rate of the user, and a heart rate of the user.

15. The method of claim 1, wherein the graphical representations of buttons includes graphical representations of at least one of a power button, an air flow mode button, a "+" button, and a "−" button.

16. The method of claim 1 further comprising the step of simulating certain conditions to diagnose a problem.

17. The method of claim 16 where the simulating is performed by system software run by the computing-based device.

18. The method of claim 1 further comprising the step of adjusting a parameter of the respiratory care device using a hidden button on the respiratory care device that is not labeled and that does not otherwise provide an indication of functionality before actuation.

* * * * *